(12) United States Patent
Novokhatny

(10) Patent No.: US 8,512,980 B2
(45) Date of Patent: Aug. 20, 2013

(54) RECOMBINANTLY MODIFIED PLASMIN

(75) Inventor: Valery Novokhatny, Raleigh, NC (US)

(73) Assignee: Grifols Therapeutics Inc., Research Triangle Park, NC (US)

( * ) Notice: Subject to any disclaimer, the term of this patent is extended or adjusted under 35 U.S.C. 154(b) by 0 days.

(21) Appl. No.: 13/463,437

(22) Filed: May 3, 2012

(65) Prior Publication Data

US 2012/0276611 A1 Nov. 1, 2012

Related U.S. Application Data

(60) Continuation of application No. 13/302,322, filed on Nov. 22, 2001, now Pat. No. 8,182,808, which is a division of application No. 12/744,376, filed as application No. PCT/US2008/084645 on Nov. 25, 2008, now Pat. No. 8,101,394.

(60) Provisional application No. 60/991,148, filed on Nov. 29, 2007.

(51) Int. Cl.
*C12P 21/06* (2006.01)
*C12N 9/50* (2006.01)
*A61K 35/14* (2006.01)

(52) U.S. Cl.
USPC .......... 435/68.1; 435/219; 435/6.19; 530/380

(58) Field of Classification Search
None
See application file for complete search history.

(56) References Cited

U.S. PATENT DOCUMENTS

| | | |
|---|---|---|
| 4,631,211 A | 12/1986 | Houghten et al. |
| 4,652,639 A | 3/1987 | Stabinsky |
| 4,774,087 A | 9/1988 | Wu et al. |
| 6,218,517 B1 | 4/2001 | Suzuki |
| 6,312,893 B1 | 11/2001 | Van Ness et al. |
| 6,355,243 B1 | 3/2002 | Novokhatny et al. |
| 6,444,422 B2 | 9/2002 | Van Ness et al. |
| 6,538,103 B1 | 3/2003 | Ji et al. |
| 6,613,508 B1 | 9/2003 | Ness et al. |
| 6,623,928 B2 | 9/2003 | Van Ness et al. |
| 6,664,112 B2 | 12/2003 | Mulligan et al. |
| 6,946,438 B1 | 9/2005 | Nagai et al. |
| 6,964,764 B2 | 11/2005 | Zimmerman et al. |
| 6,969,515 B2 | 11/2005 | Jesmok et al. |
| 7,253,264 B1 | 8/2007 | Lauffler et al. |
| 2003/0012778 A1 | 1/2003 | Zimmerman |
| 2003/0147877 A1 | 8/2003 | Trese et al. |
| 2005/0118158 A1 | 6/2005 | Pakola et al. |
| 2005/0124036 A1 | 6/2005 | Susilo et al. |

FOREIGN PATENT DOCUMENTS

| | | |
|---|---|---|
| WO | WO 97/27331 A2 | 7/1997 |
| WO | WO 99/05322 A1 | 2/1999 |
| WO | WO 01/94366 A1 | 12/2001 |
| WO | WO 02/50290 A1 | 6/2002 |
| WO | WO 03/054232 A2 | 7/2003 |
| WO | WO 2004/52228 A2 | 6/2004 |
| WO | WO 2005/105990 A2 | 11/2005 |
| WO | WO 2007/047874 A2 | 4/2007 |
| WO | WO 2009/073471 A1 | 6/2009 |

OTHER PUBLICATIONS

Andrianov, S.I., et al., "Peculiarities of Hydrolytic Action of Plasmin, Miniplasmin, Microplasmin and Trypsin on Polymeric Fibrin," *Ukr. Biokhim. Zh.*, 64(3): 14-20 (1992).
Anonick, P., of al., "Regulation of Plasmin, Miniplasmin and Streptokinase—Plasmin Complex by—a-2-Antiplasmin, a-2-Macroglobulin, and Antithrombin III in the Presence of Heparin," *Thrombosis Res.*, 59: 449-462 (1990).
Bennett, D., et al., "Kinetic Characterization of the Interaction of Biotinylated Human Interleukin 5 with an Fc Chimera of its Receptor a Subunit and Development of an ELISA Screening Assay using Real-Time Interaction Biosensor Analysis," *J. Molecular Recognition*, 8: 52-58 (1995).
Bhisitkul, R.B., "Anticipation for enzymatic vitreolysis," *Br. J. OphthalmoL*, 85: 1-3 (2001).
Bowie, J.U., et al., "Deciphering the Message in Protein Sequences: Tolerance to Amino Acid Substitutions," *Science*, 247: 1306-1310 (1990).
Burck, P.J., et al., "Characterization of a Modified Human Tissue Plasminogen Activator Comprising a Kringle-2 and a Protease Domain,"*J. Biol. Chem.*, 265(9): 5170-5177 (1990).
Burgin, J. and J. Shaller, "Expression, Isolation and Characterization of a Mutated Human Plasminogen Kringle 3 with a Functional Lysine Binding Site," *Cell. Mol. Life. Sci.* 55: 135-141 (1999).
Cao, Y., et al., "Kringle Domains of Human Angiostatin," *J. Biol. Chem.*, 271(46): 29461-29467 (1996).
Castellino, F.J., and S.G. McCance, "The kringle domains of human plasminogen," *Ciba Found. Symp.*, 212: 46-65 (1997).
Chang, Y., et al., "Structure and Ligand Binding Determinants of the Recombinant Kringle 5 Domain of Human Plasminogen," *Biochemistry*, 37: 3258-3271 (1998).
Chase, T. and E. Shaw, "Titration of Trypsin, Plasmin, and Thrombin with p-Nitrophenyl 0-Guanidinobenzoate HCI," *Methods EnzymoL*, 19: 20-27 (1970).
Christensen, S., et al., "Stopped-Flow Fluorescence Kinetics of Bovine α2-Antiplasmin Inhibition of Bovine Midiplasmin," *Biochem. J.* 305:97-102 (1995).
Cunningham, B.C., and J.A. Wells, "High-Resolution Epitope Mapping of hGH-Receptor Interactions by Alanine-Scanning Mutagenesis," *Science*, 244: 1081-1085 (1989).
de Vos, A.M., et al., "Human Growth Hormone and Extracellular Domain of Its Receptor: Crystal Structure of the Complex," *Science*, 255: 306-312 (1992).
Deutsch, D.G and E. T. Mertz, "Plasminogen Purification from Human Plasma by Affinity Chromatography," *Science* 107:1095-1096 (1970).

(Continued)

*Primary Examiner* — Nashaat Nashed
(74) *Attorney, Agent, or Firm* — Womble Carlyle Sandridge & Rice, LLP

(57) ABSTRACT

Polynucleotides and polypeptides relating to a recombinantly modified plasmin(ogen) molecule are provided. The plasmin(ogen) molecule has a single kringle domain N-terminal to the activation site present in the native human plasminogen molecule, combined such that no foreign sequences are present, and exhibits lysine-binding and significant enzymatic characteristics associated with the native enzyme.

19 Claims, 7 Drawing Sheets

(56) References Cited

OTHER PUBLICATIONS

Douglas, J.T., et al., "The Two-Domain NK1 Fragment of Plasminogen: Flding, Ligand Binding, and Thermal Stability Profile," *Biochemistry*, 41(10): 3302-3310 (2002).

Gandorfer, A., et al., "Posterior Vitreous Detachment Induced by Microplasmin," *OVS*, 45(2): 641-641 (2004).

Gandorfer, A., et al., "Ultrastructure of the viteoretinal interface following plasmin assisted vitrectomy," *Br. J. Ophthalmol.*, 85: 6-10 (2001).

Goretzki, L., et al., "Binding of the NG2 Proteoglycan to Kringle Domains Modulates the Functional Properties of Angiostatin and Plasmin(ogen)," *J. Biol. Chem.*, 275(37): 2862528633 (2000).

Gribskov, M., and Richard R. Burgess, "Sigma factors from *E. coli, B. subtilis*, phage SP01, and phage T4 are homologous proteins," *Nucl. Acids Res.*, 14(6): 6745-6763 (1986).

Hoover, G.J., et al., "Amino Acids of the Recombinant Kringle 1 Domain of Human Plasminogen that Stabilize Its Interaction with w-Amino Acids," *Biochemistry*, 32(41): 10936-10943 (1993).

Horrevoets, A.J.G., et al., "Production and Characterization of Recominant Human Plasminogen (S741C-Fluorescein): A Novel Approach to Study Zymogen Activation Without Generation of Active Protease," *J. Bio. Chem.*, 272(4): 2176-2182 (1997).

Horrevoets, A.J.G., et al., The Activation-resistant Comformation of Recombinant Human Plasminogen Is Stabilized by Basic Residues in the Amino-terminal Hinge Region, *J. Bio. Chem.*, 270(26): 15770-15776 (1995).

Houghten, R.A., "General method for the rapid solid-phase synthesis of large numbers of peptides: Specificity of antigen-antibody interaction at the level of individual amino acids," *Proc. Natl. Acad. Sci. USA*, 82: 5131-5135 (1985).

Hunt and Novokhatny, *Journal of Thrombosis and Haemostasis* 2005; 3(1): Abstract No. P0781, for 20th International Society on Thrombosis and Haemostasis Congress, Sydney, Australia.

Hunt and Novokhatny, Poster presented Tuesday, Aug. 9, 2005 at 20th International Society on Thrombosis and Haemostasis Congress, Sydney, Australia.

International Search Report (PCT/US05/013562, dated Nov. 3, 2005).

International Search Report (PCT/US06/040940, dated Oct. 18, 2006).

Johanson, K., et al., "Binding Interactions of Human Interleukin 5 with Its Receptor a Subunit," *J. Biol. Chem.*, 270(16): 9459-9471 (1995).

Kolev, K., et al., "Functional Evaluation of the Structural Features of Proteases and Their Substrate in Fibrin Surface Degradation," *J. Biol. Chem.*, 272(21): 13666-75 (1997).

Komorowicz, E., et al., "Fibrinolysis with Des-Kringle Derivatives of Plasmin and Its Modulation by Plasma Protease Inhibitors," *Biochemistry*, 37(25): 9112-9118 (1998).

Langer-Safer, P.R., et al., "Replacement of Finger and Growth Factor Domains of Tissue Plasminogen Activator with Plasminogen Kringle 1," *J. Biol. Chem.* 265(6):3715-3723 (1991).

Lee, H., et al., "Disruption of Interkringle Disulfide Bond of Plasminogen Kringle 1-3 Changes the Lysine Binding Capability of Kringle 2, But Not Its Antiangiogenic Activity," *Arch. Biochem. Biophys.*, 375(2): 359-363 (2000).

Lerch, P.G., et al., "Localization of Individual Lysine-Binding Regions in Human Plasminogen and Investigations on Their Complex-Forming Properties," *Eur J. Biochem.*, 107(1): 7-13 (1980).

Li, X., et al., "Posterior Vitreous Detachment with Plasmin in the Isolated Human Eye," *Graefe's Arch, Clin. Exp. Ophthalmot*, 240:56-62 (2002).

Lin, L-F., et al., "Epsilon Amino Caproic Acid Inhibits Streptokinase—Plasminogen Activator Complex Formation and Substrate Binding through Kringle-Dependent Mechanisms," *Biochemistry*, 39: 4740-4745 (2000).

Lucas, M.A., et al., "The Binding of Human Plasminogen to Fibrin and Fibrinogen," *J. Biol. Chem.*, 258(7): 4249-4256 (1983).

Madison, E.L., "Probing Structure-Function Relationships of Tissue-Type Plasminogen Activator by Site-Specific Mutagenesis," *Fibrinolysis* 8 Supp.1:221-236 (1994).

Marder, V.J., et al., "Plasmin Induces Local Thrombolysis without Causing Hemorrhage: A Comparison with Tissue Plasminogen Activator in the Rabbit," *Thromb. Haemost.*, 86(3): 739745 (2001).

Matsuka, Y.V., et al., "Fluorescence spectroscopic analysis of ligand binding to kringle 1+2+3 and kringle 1 fragments from human plasminogen," *Eur. J. Biochem.*, 190: 93-97 (1990).

McCance, S., et al., "Amino Acid Residues of the Kringle-4 and Kringle-5 Domains of Human Plasminogen that Stabilize their Interactions with w-Amino Acid Ligands," *J. Biol. Chem.*, 269(51): 32405-32410 (1994).

Medynski, D., et al., "Refolding, purification, and activation of miniplasminogen and microplasminogen isolated from *E. coli* inclusion bodies," *Protein Expression and Purification* 52:395-402 (2007).

Menhart, N., of al., "Functional Independence of the Kringle 4 and Kringle 5 Regions of Human Plasminogen," *Biochemistry*, 32: 8799-8806 (1993).

Motta, A., of al., "Complete Assignment of the Aromatic Proton Magnetic Resonance Spectrum of the Kringle 1 Domain from Human Plasminogen: Structure of the Ligand-Binding Site," *Biochemistry*, 26(13): 3827-3836 (1987).

Mukhopadhyay, A., "Inclusion Bodies and Purification of Proteins in Biologically Active Forms," *Advances in Bio. Eng./Biotech.* 56:61-109 (1997).

Novokhatny, V., and Stanislav A. Kudinov, "Domains in Human Plasminogen," *J. MoL Biol.*, 179: 215-232 (1984).

Novokhatny, V., at al., "Analysis of Ligand Binding to Kringles 4 and 5 Fragments from Human Plasminogen," *Thromb Res.*, 53(3): 243-52 (1989).

Novokhatny, V., et al., "Thrombolytic potency of add-stabilized plasmin: superiority over tissue-type plasminogen activator in an in vitro model of catheter-assisted thrombolysis," *J. Thromb. Haemost.*, 1(5): 1034-1041 (2003).

Novokhatny, V., et al., "Domain Structure and Domain-Domain Interaction of recombinant Tissue Plasminogen Activator," *J. Biol. Chem.* 266(20):12994-13002 (1991).

Obukowicz, M.G., et al., "Secretion of Active Kringle-2—Serine Protease in *Escherichia coli,*" *Biochemistry* 29:9737-9745 (1990).

Patthy, L., et al., "Evolution of the Proteases of Blood Coagulation and Fibrinolysis by Assembly from Modules," *Cell* 41:657-663 (1985).

Powell, J.R., and Francis J. Castellino, "Activation of Human Neo-Plasminogen-Va1442 by Urokinase and Streptokinase and a Kinetic Characterization of Neo-Plasmin-Va1442," *J. Biol. Chem.*, 255(11): 5329-5335 (1990).

Rejante, M.R. and M. Llinas, "Solution structure of the e-aminohexanoic acid complex of human plasminogen kringle 1," *Eur. J. Biochem.*, 221(3): 939-949 (1994).

Schwartz, R.M. and M.O. Dayhoff, "Matrices for Detecting Distant Relationships," *Atlas of Protein Sequence and Structure*, 5(3): 353-358 (1978).

Shi, G-Y., et al., "Kringle Domains and Plasmin Denaturation," *Biochem. Biophys. Res. Comm.*, 178(1): 360-368 (1991).

Smith, L.J., et al., "Human Interleukin 4: The Solution Structure of a Four-helix Bundle Protein," *J. Mol. Biol.*, 224: 899-904 (1992). 1.

Smith, T.F., and Michael S. Waterman, "Comparison of Biosequences," *Advances in Applied Mathematics*, 2: 482-489 (1981).

Söhndel, S., et al., "Recombinant Gene Expression and 1H NMR characteristics of the Kringle (2+3) Supermodule: Spectroscopic/Functional Individuality of Plasminogen Kringle Domains," *Biochemistry* 35:2357-2364 (1996).

Sottrup-Jensen, L, of al., "The Primary Structure of Human Plasminogen: Isolation of Two Lysine-Binding Fragments and One "Mini-" Plasminogen (MW, 38,000) by Elastase-CatalyzedSpecific Limited Proteolysis," *Prog. Chem. Fibrinol. ThromboL*, 3: 191-209 (1978).

Stewart, D., of al., "Distinct dose-dependent effects of plasmin and TPA on coagulation and hemorrhage," *Blood*, 101(8): 3002-3007 (2003).

Thewes, T., of al., "Ligand Interactions with the Kringle 5 Domain of Plasminogen," *J. Biol. Chem.*, 265(7): 3906-3915 (1990).

Trese, M.T., "Enzymatic Vitreous Surgery," *Seminars in Ophthalmology*, 15(2): 116-121 (2000)1.

Van Zonneveld, A-J., of al., "Autonomous functions of structural domains on human tissue-type plasminogen activator," *PNAS*, 83: 4670-4674 (1986).

Verstraeten, T.C., et al., "Pharmacologic Induction of Posterior Vitreous Detachment in the Rabbit," *Arch Ophthalmol.*,, 111: 849-854 1993.

Wang, F., et al., "Safety and Efficacy of Displase and Plasmin in Pharmacologic Vitreolysis," *OVS*, 45(9): 3286-3290 (2004).

Wang, J., et al., "Structure and Function of Microplasminogen: I. Methionine Shuffling, Chemical Proteolysis, and Proenzyme Activation," *Protein Sci.* 4:1758-1767 (1995).

Wang, S., et al., "Deletion of lie 1 Changes the Mechanism of Streptokinase: Evidence for Molecular Sexuality Hypothesis," *Biochemistry* 38: 5232-5240 (1999).

Wang, Z-L, et al., "PVD Following Plasmin But Not Hyaluronidase: Implications for Combination Pharmacologic Vitreolysis Therapy," *Retina*, 25: 38-43 (2005).

Williams, J.G., et al., "Autologous Plasmin Enzyme in the Surgical Management of Diabetic Retinopathy," *Ophthalmology* 108(10): 1902-1905 (2001).

Wiman, B. and Dêsirê Collen, "On the Kinetics of the Reaction between Human Antiplasmin and Plasmin," *Eur. J. Biochem.*, 84: 573-578 (1978).

Wiman, B. and Dêsire Collen, *Nature*, 272: 549-550 (1978).

Wiman, B., et al., "On the Specific Interaction Between the Lysine-Binding Sites in Plasmin and Complementary Sites in a2—Antiplasmin and in Fibrinogen," *Biochim. Biophys. Acta*, 579: 142-154 (1979).

Wohl, R.C., et al., "Kinetics of Activation of Human Plasminogen by Different Activator Species at pH 7.4 and 37° C," *J. Biol. Chem.*, 255(5): 2005-2013 (1980).

Wohl, R.C., et al., "Steady State Kinetics of Activation of Human and Bovine Plasminogens by Streptokinase and Its Equimolar Complexes with Various Activated Forms of Human Plasminogen,"*J. Biol. Chem.*, 253(5): 1402-1407 (1978).

Wu, S-C., et al., A Fast-Acting Modular-Structured Staphylokinase Fusion with Kringle-1 From Human Plasminogen as the Fibrin-Targeting Domain Offers Improved Clot Lysis Efficacy, *J. Biol. Chem.* 278(20):18199-181206 (2003).

Wu, T P. et al., "The structure of recombinant plasminogen kringle 1 and the fibrin binding site," *Blood CoaguL Fibrinolysis*, 5(2): 157-166 (1994).

Zajicek, J., et al., "The Effects of Ligand Binding on the Backbone Dynamics of the Kringle 1 Domain of Human Plasminogen," *J. MoL Biol.*, 301(2): 333-347 (2000).

Plasmin (TAL6003)-plasminogen

FIG. 3

```
 -19              1
MEHKEVVLLLLLFLKSGQGEPLDDYVNTQGASLFSVTKKQLGAGSIEECAAKCEEDEEFTCRAFQ

78
YHSKEQQCVIMAENRKSSIIIRMRDVVLFEKKVYLSECKTGNGKNYRGTMSKTKNGITCQKWSS 136       143       153       162
SPHRPRFSPATHPSEGLEENYCRNPDNDPQGPWCYTTDPEKRYDYCDILECEEECMHCSGENYDG
         kringle 1

234
KISKTMSGLECQAWDSQSPHAHGYIPSKFPNKNLKKNYCRNPDRELRPWCFTTDPNKRWELCDIP
              kringle 2

RCTTPPPSSGPTYQCLKGTGENYRGNVAVTVSGHTCQHWSAQTPHTHNRTPENFPCKNLDENYCR
                                                       kringle 3

324
NPDGKRAPWCHTTNSQVRWEYCKIPSCDSSPVSTEQLAPTAPPELTPVVQDCYHGDGQSYRGTSS

426
TTTTGKKCQSWSSMTPHRHQKTPENYPNAGLTMNYCRNPDADKGPWCFTTDPSVRWEYCNLKKCS
                 kringle 4

GTEASVVAPPPVVLLPDVETPSEEDCMFGNGKGYRGKRATTVTGTPCQDWAAQEPHRHSIFTPET
                                                         kringle 5

532       542                       561
NPRAGLEKNYCRNPDGDVGGPWCYTTNPRKLYDYCDVPQCAAPSFDCGKPQVEPKKCPGRVVGGC

VAHPHSWPWQVSLRTRFGMHFCGGTLISPEWVLTAAHCLEKSPRPSSYKVILGAHQEVNLEPHVQ

EIEVSRLFLEPTRKDIALLKLSSPAVITDKVIPACLPSPNYVVADRTECFITGWGETQGTFGAGL

LKEAQLPVIENKVCNRYEFLNGRVQSTELCAGHLAGGTDSCQGDSGGPLVCFEKDKYILQGVTSW

791
GLGCARPNKPGVYVRVSRFVTWIEGVMRNN     (SEQ ID NO:4)
```

FIG. 4

```
HK1    CKTGNGKNYR  GTMSKTKNGI  TCQKWSSTSP  HR-PRFSPAT  HPSEGLEENY
HK2    CMHCSGENYD  GKISKTMSGL  ECQAWDSQSP  HA-HGYIPSK  FPNKNLKKNY
HK3    CLKGTGENYR  GNVAVTVSGH  TCQHWSAQTP  HT-HNRTPEN  FPCKNLDENY
HK4    CYHGDGQSYR  GTSSTTTTGK  KCQSWSSMTP  HR-HQKTPEN  YPNAGLTMNY
HK5    CMFGNGKGYR  GKRATTVTGT  PCQDWAAQEP  HRHSIFTPET  NPRAGLEKNY (con't)
HK1    CRNPDNDPQG  PWCYTTDPEK  RYDYCDILEC  (SEQ ID NO:6)
HK2    CRNPDRE-LR  PWCFTTDPNK  RWELCDIPRC  (SEQ ID NO:7)
HK3    CRNPDGK-RA  PWCHTTNSQV  RWEYCKIPSC  (SEQ ID NO:8)
HK4    CRNPDAD-KG  PWCFTTDPSV  RWEYCNLKKC  (SEQ ID NO:9)
HK5    CRNPDGDVGG  PWCYTTNPRK  LYDYCDVPQC  (SEQ ID NO:10)
```

FIG.10

```
  1 M(X)KVYLSE CKTGNGKNYRGTMSKTKNGIT    CQKWSSTSPHRPRFSPATHPSE

59 GLEENY CRNPDNDPQGPW CYTTDPEKRYDY CDVPQ CAAPSFD CGKPQVEP

109 KK CPGRVVGG CVAHPHSWPWQVSLRTRFGMHF  CGGTLISPEWVLTAAH  CL

159 EKSPRPSSYKVILGAHQEVNLEPHVQEIEVSRLFLEPTRKDIALLKLSSP

209 AVITDKVIPA CLPSPNYVVADRTE CFITGWGETQGTFGAGLLKEAQLPVI

259 ENKV CNRYEFLNGRVQSTEL CAGHLAGGTDS CQGDSGGPLV CFEKDKYIL

309 QGVTSWGLG CARPNKPGVYYRVSRFVTWIEGVMRNN
                         X=RDVVLFEK
```

(See SEQ ID NO: 2)

RECOMBINANTLY MODIFIED PLASMIN

RELATED APPLICATIONS

This application is a continuation of U.S. patent application Ser. No. 13/302,322, filed Nov. 22, 2011 now U.S. Pat. No. 8,182,808, which is a divisional of U.S. patent application Ser. No. 12/744,376, filed Sep. 16, 2010 now U.S. Pat. No. 8,101,394, which is a national phase application under 35 U.S.C. §371 of International Application Serial No. PCT/US08/84645, filed Nov. 25, 2008, that claims benefit of priority under 35 U.S.C. §119 to U.S. Provisional Application No. 60/991,148, filed Nov. 29, 2007, the contents of each which are hereby incorporated by reference in their entirety.

BACKGROUND OF THE INVENTION

Human plasminogen is a single-chain protein containing 791 amino acid residues. Activation of plasminogen to plasmin results from a single cleavage of the Arg561-Val562 peptide bond in the zymogen. The resulting plasmin molecule is a two-chain, disulfide-linked serine protease with trypsin-like specificity (cleaves after Lys and Arg).

The amino-terminal heavy chain of plasmin (residues 1-561, ~60 kDa) is composed of five kringle domains, each containing approximately 80 amino acid residues. The kringle domains are responsible for the regulatory properties of plasminogen, such as interaction with activation inhibitors, e.g., $Cl^{-1}$ ions; with activation stimulators, e.g., $\epsilon$-aminocaproic acid; with mammalian and bacterial cells; and with other proteins, such as the plasmin physiological substrate, fibrin and plasmin inhibitor, $\alpha$2-antiplasmin. Of all five kringles, kringle 1 is one of the most multi-functional: its lysine-binding activity has been shown to be responsible for plasmin interaction with $\alpha$2-antiplasmin and fibrin. See Wiman, B., et al., *Biochim. Biophys. Acta* 579: 142-154 (1979); and Lucas, M. A., et al., *J. Biol. Chem.* 258: 4249-4256 (1983).

The C-terminal light chain of plasmin (residues 562-791, ~25 kDa) is a typical serine protease, homologous to trypsin and containing the classic serine protease catalytic triad: His603, Asp646 and Ser741. Plasminogen contains 24 disulfide bridges and 2 glycosylation sites on Asn289 and Thr346.

The limited proteolysis of plasminogen by elastase has been shown to result in three major fragments (Sottrup-Jensen, L., et al., *Prog. Chem. Fibrinol. Thrombol.* 3: 191-209 (1978)). First fragment, K1-3, includes the first three kringles and can be isolated in two versions, Tyr80-Val338 and Tyr80-Val354. The second fragment, K4, corresponds to the fourth kringle and includes residues Val355-Ala440. The last, C-terminal fragment (the so-called mini-plasminogen) includes residues Val443-Asn791 and consists of the fifth kringle and the serine protease domain. Mini-plasminogen can be activated in the same way as plasminogen, forming mini-plasmin.

Because of the complex structure of the full-length plasminogen molecule, bacterial expression systems have not proven useful for recombinant plasminogen production. Plasminogen is produced in the form of insoluble inclusion bodies and is not re-foldable from that state. Further, the expression of plasminogen in mammalian cells is complicated by intracellular activation of plasminogen into plasmin and the resulting cytotoxicity. Production of fully active plasminogen using insect cells is possible, however, this system is not suitable for large-scale production due to low yield. Further, as with any recombinant protein scheme, the potential exists for encountering immunogenicity problems in the subject receiving the therapeutic recombinant protein.

Immunogenicity can be a barrier to the effective and/or efficient utilization of certain recombinant protein therapeutic schemes. Immunogenicity is a complex series of responses to a substance (e.g., the chemical structure of a protein including the amino acid sequence) that is perceived as foreign and may include production of neutralizing and non-neutralizing antibodies, formation of immune complexes, complement activation, mast cell activation, inflammation, and anaphylaxis. Immunogenicity may limit the efficacy and safety of a protein therapeutic in multiple ways. Efficacy can be reduced directly by the formation of neutralizing antibodies. Efficacy may also be reduced indirectly, as binding to either neutralizing or non-neutralizing antibodies typically leads to rapid clearance from serum. Severe side effects and even death may occur when an immune reaction is raised. One special class of side effects results when neutralizing antibodies cross-react with an endogenous protein and block its function.

Accordingly, a modified recombinant protein, possessing the desirable characteristics (e.g., regions with native-like chemical structures) of plasmin/plasminogen while lacking certain negative characteristics and being capable of production in recombinant protein expression systems including bacterial cells in substantial quantities, is desirable.

SUMMARY OF THE INVENTION

In one aspect, the present invention provides a polynucleotide comprising a nucleotide sequence encoding a polypeptide having:
 (a) a single N-terminal kringle domain homologous to a kringle domain of native human plasminogen, wherein the last four amino acid residues within the kringle domain are V, P, Q, and C; and
 (b) a C-terminal domain activation site and serine protease domain homologous to the corresponding domains in human plasminogen; wherein the polypeptide binds to immobilized lysine.

In another aspect, the present invention provides a polypeptide comprising:
 (a) a single N-terminal kringle domain homologous to a kringle domain of native human plasminogen, wherein the last four amino acid residues within the kringle domain are V, P, Q, and C; and
 (b) a C-terminal domain activation site and serine protease domain homologous to the corresponding domains in human plasminogen; wherein the polypeptide binds to immobilized lysine.

In other aspects, the present invention provides an expression vector comprising a polynucleotide of the present invention. In one embodiment, the polynucleotide comprises a nucleotide sequence as shown in SEQ ID NO: 1.

In some aspects, the present invention provides a cultured cell comprising an expression vector comprising a polynucleotide of the present invention. In one embodiment, the polynucleotide comprises a nucleotide sequence as shown in SEQ ID NO: 1. In another embodiment, the cultured cell is a prokaryotic organism. In one embodiment, the prokaryotic organism is *E. coli*.

In one aspect, the present invention provides a method for making one or more recombinant plasmin polypeptides. The method comprises:
 (a) providing a polypeptide having a single N-terminal kringle domain homologous to a kringle domain of native human plasminogen, wherein the last four amino acid residues within the kringle domain are V, P, Q, and C; and a C-terminal domain activation site and serine protease domain homologous to the corresponding domains in human plasminogen; wherein the polypeptide binds to immobilized lysine; and (b) contacting the polypeptide provided in step a) with a protease under conditions sufficient to cleave one or more peptide bonds thereby forming the one more recombinant plasmin polypeptides. In one embodiment, providing comprises expressing an open reading frame having a sequence corresponding to the sequence as shown in SEQ ID NO: 1, or a degenerate variant thereof, in a suitable host. In another embodiment, the polypeptide has an amino acid sequence as shown in SEQ ID NO: 2.

BRIEF DESCRIPTION OF THE DRAWINGS

FIG. 3 shows the amino acid sequence of human plasminogen, showing the 19-residue leader sequence numbered as −19 to −1, and the plasminogen sequence shown as residues 1-791 (see SEQ ID NO: 3, the cDNA sequence for human plasminogen; and SEQ ID NO: 4, the encoded amino acid sequence, as shown in FIG. 3). A number of features are shown, including the following: one embodiment of the (TAL6003)-plasminogen sequence (shaded); kringle domains 1-5 (double underscore); glycosylations sites Asn289 and Thr346 (in bold); the Arg-Val activation site (R561-V562 in bold); and lysine-binding sites in kringle 1 (in underscore and with specific position numbering).

FIG. 4 shows polypeptide sequence comparisons (i.e., a gap alignment) between the five kringle domains (1-5) of native human plasmin(ogen). Amino acid residues that are identical to those of the same relative position in kringle 1 are shown in underscore.

FIG. 10 illustrates disulfide bonding pattern of (TAL6003)-plasmin (SEQ ID NO: 2). In the figure, (X) represents the amino acid sequence RDVVLFEK.

DESCRIPTION OF THE INVENTION

Figure 1:
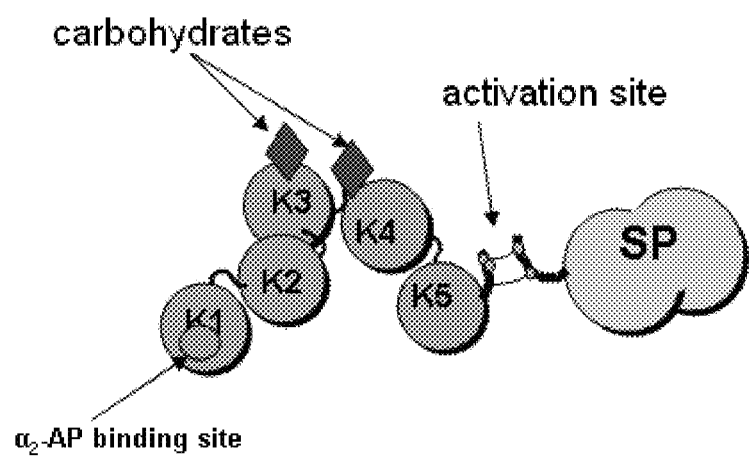
FIG. 1 is a schematic representation of native plasmin after activation by proteolytic cleavage. K1-K5 are kringle regions 1-5; and SP is the serine protease domain. "α2-AP" is the α2-antiplasmin binding site on kringle 1.
Figure 2:
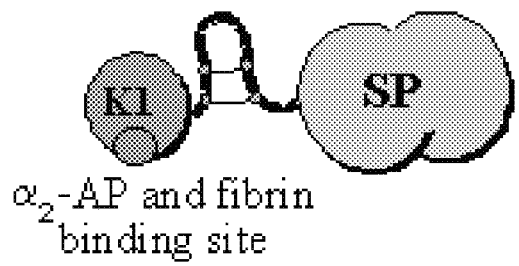
FIG. 2 is a schematic representation of a plasminogen deletion mutant of the invention using the same nomenclature as in FIG. 1, and showing the deletion of K2-5.
Figure 5:
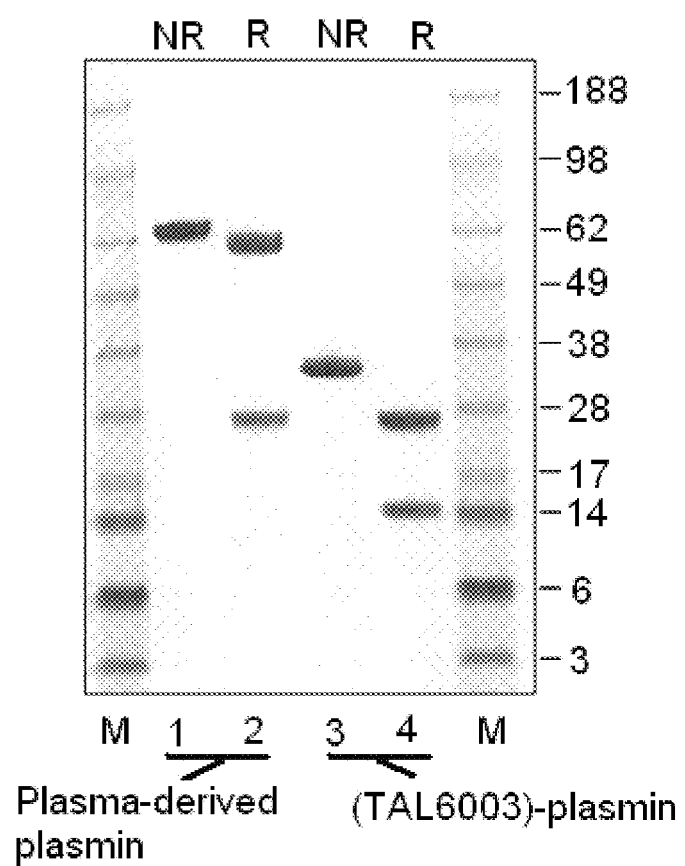
FIG. 5 shows a 8-25% gradient SDS-PAGE of plasma-derived plasmin (Lane 1=non-reduced (NR); Lane 2=reduced (R)) and (TAL6003)-plasmin (Lane 3=non-reduced (NR); Lane 4=reduced (R)) preparation. Streptokinase activation of plasma-derived plasminogen and (TAL6003)-plasminogen into native plasmin and recombinant (TAL6003)-plasmin, respectively, results in the formation of two bands corresponding to the kringle and the serine protease domains. Accordingly, following incubation with the reducing agent dithiothreitol (DTT) prior to electrophoresis, plasma-derived plasmin and (TAL6003)-plasmin, which are a single band on a non-reduced gel, reduce to two bands corresponding to kringle 1 (lower band) and the serine protease domain (upper band) in the same non-reduced gel.

The present inventors have discovered novel recombinant plasminogen polypeptides, or variants thereof, herein referred to as (TAL6003)-plasminogens that have native plasminogen-like features despite deletion of 4 kringles from its structure. These (TAL6003)-plasminogens, or variants thereof, are zymogens that are capable of becoming activated to functional plasmin enzymes (herein referred to as (TAL6003)-plasmins) following an activation event that at least involves proteolytic cleavage of an Arg-Val peptide bond located between the kringle domain and the serine protease domain of the zymogen.

The (TAL6003)-plasminogen, or a variant thereof, of the present invention has fibrin- and antiplasmin-binding as well as activation properties of full-length native human plasminogen. Further, the (TAL6003)-plasminogen has a number of novel and desirable features including high-level expression in recombinant production and certain protein chemical structures identical or very similar to naturally occurring forms of human plasma-derived plasminogen.

The (TAL6003)-plasmin(ogen)s according to the present invention can be characterized at least by the following:

(i) the lower molecular weights (e.g., in one embodiment about 36,911 to about 37,039 Da) of (TAL6003)-plasmins created following activation of (TAL6003)-plasminogens result in increased specific activity (per mg of protein);

(ii) the lack of at least two glycosylation sites found in the native protein (see FIG. 3, i.e., N289 and T346), combined with the relatively low molecular weights, facilitates recombinant production of this protein using relatively inexpensive bacterial and yeast expression systems;

(iii) (TAL6003)-plasminogens can be activated by plasminogen activators tPA, urokinase, and streptokinase;

(iv) the presence of the single N-terminal kringle domain homologous to a kringle domain of native human plasminogen preserves the fibrin-binding properties of plasmin which are important for thrombolytic efficacy;

(v) the presence of α2-antiplasmin-binding sites on the single N-terminal kringle domain homologous to a kringle domain of native human plasminogen allows the (TAL6003)-plasmins to be inhibited rapidly by this physiological inhibitor of plasmin (a feature which can prevent bleeding);

(vi) the smaller size of the (TAL6003)-plasmins can facilitate their inhibition by α2-macroglobulin, further lessening the chance of bleeding complications relative to native plasmin. In particular embodiments, the absence of kringle 5, which retains the primary binding site for intact, undigested fibrin(ogen), can allow use of the (TAL6003)-plasmins with reduced depletion of circulating fibrinogen;

(vii) the presence of a single N-terminal kringle domain homologous to a kringle domain of native human plasminogen, wherein the last four amino acid residues within the kringle domain are V, P, Q, and C, provides a native-like linkage to the serine protease domain (i.e., a linkage similar to the naturally occurring domain juncture between the kringle 5 domain and the serine protease domain of human plasminogen); and (viii) following expression of the recombinant (TAL6003)-plasminogen, its N-terminus may be cleaved back (e.g., cleaved back during activation) to provide a native-like N-terminus.

Generally, the invention provides recombinant (TAL6003)-plasmin(ogen) polypeptides having a single kringle region N-terminal to the activation site and serine protease domain, having certain advantages relative to mini-plasmin (ogen). Although the (TAL6003)-plasminogens of the invention only have one kringle domain, as such, N-terminal to the activation site, some embodiments include additional sequences N-terminal to the activation site. Additional N-terminal sequences can be derived from those of native kringle regions of plasminogen.

The N-terminal kringle domains of the present invention include kringle sequences of kringles 1 and 4 of native plasmin(ogen) and functional equivalents thereof. In particular, see the discussion below that provides guidance regarding preservation of function in polypeptide variants, including preservation of residues participating in or influencing lysine binding.

Further, particular embodiments of the polypeptides of the present invention can exhibit reduced immunogenicity by virtue of native-like structures. For example, in some embodiments, the recombinant plasminogen of the present invention has an N-terminus identical to that of one of the naturally occurring forms of human plasma-derived plasminogen, which upon activation by streptokinase, produces plasmin polypeptides comprising native-like N-termini. Additionally, the novel polypeptides of the present invention have a sequence between the Kringle and Serine protease domains that is similar to the junction between Kringle 5 and the SP domain in naturally occurring human plasmin.

Definitions

The terms "domain" and "region" of a polypeptide are generally synonymous as used herein, unless otherwise indicated to the contrary. When recited together with well-recognized structural or functional designations such as "kringle" or "serine protease," etc., such terms will introduce a polypeptide feature relating to at least some characteristic(s) commonly recognized and understood to be associated with the polypeptide structures corresponding to such designations.

A "cultured host cell," as used herein, refers to a prokaryotic or eukaryotic cell that contains heterologous DNA that has been introduced into the cell by any means, e.g., electroporation, calcium phosphate precipitation, microinjection, transformation, viral infection, and the like.

"Heterologous" as used herein means "of different natural origin" or representing a non-natural state. For example, if a cultured host cell is transformed with a DNA or gene derived from another organism, particularly from another species, that gene is heterologous with respect to that cultured host cell, and also with respect to descendants of the cultured host cell which carry that gene. Similarly, "heterologous" refers to a nucleotide sequence derived from and inserted into the same natural, original cell type, but which is present in a non-natural state, e.g., a different copy number or under the control of different regulatory elements. Further, when used in the context of a nucleic acid or amino acid sequence, the term "heterologous" also may refer to any region of the sequence that is of a different natural origin than another region of the same sequence. For example, if a recombinant protein comprises a kringle domain derived from apolipoprotein(a) and a serine-protease domain derived from plasminogen, the kringle domain and the serine protease domain are "heterologous" relative to each other, particularly if each domain is derived from a different species or organism.

A "vector" molecule is a nucleic acid molecule into which heterologous nucleic acid can be inserted which can then be introduced into an appropriate cultured host cell. Vectors preferably have one or more origins of replication, and one or more sites into which the recombinant DNA can be inserted. Vectors often have convenient means by which cells with vectors can be selected from those without, e.g., they encode drug resistance genes. Common vectors include plasmids, viral genomes, and (primarily in yeast and bacteria) "artificial chromosomes."

As used herein, the term "transcriptional control sequence" refers to nucleic acid sequences, such as initiator sequences, enhancer sequences and promoter sequences, which induce, repress, or otherwise control the transcription of protein encoding nucleic acid sequences to which they are operably-linked.

The term "polypeptide" is used interchangeably herein with the terms "peptide" and "protein."

The terms "polynucleotide" and "nucleic acid" are used interchangeably herein, and can refer to any nucleic acid that contains the information necessary for the purpose indicated by the context. That is, the nucleic acid can be DNA or RNA, either single stranded or double stranded, or other nucleic acid, as long as the polymer is capable of representing the appropriate information, e.g., in relation to an encoded peptide, and can include complementary sequences, e.g., sense strands and anti-sense strands of nucleic acids polymers.

The term "variant" of a polypeptide refers to an amino acid sequence that is altered by one or more amino acids. The variant can have "conservative" changes, wherein a substituted amino acid has similar structural or chemical properties, e.g., replacement of leucine with isoleucine. Alternatively, a variant can have "non-conservative" changes, e.g., replacement of a glycine with a tryptophan. Analogous minor variation can also include amino acid deletion or insertion, or both. A particular form of a "variant" polypeptide is a "functionally equivalent" polypeptide, i.e., a polypeptide that exhibits substantially similar in vivo or in vitro activity as the examples of the polypeptide of invention, as described in more detail below. Guidance in determining which amino acid residues can be substituted, inserted, or deleted without eliminating biological or immunological activity can be found using computer programs well known in the art, for example, DNASTAR software (DNASTAR, Inc., Madison, Wis.). Further, specific guidance is provided below, including that provided within the cited references that are fully incorporated herein by reference.

The terms "N-terminal" and "C-terminal" are used herein to designate the relative position of any amino acid sequence or polypeptide domain or structure to which they are applied. The relative positioning will be apparent from the context. That is, an "N-terminal" feature will be located at least closer to the N-terminus of the polypeptide molecule than another feature discussed in the same context (the other feature possible referred to as "C-terminal" to the first feature). Similarly, the terms "5'-" and "3'-" can be used herein to designate relative positions of features of polynucleotides.

The polypeptides referred to herein as having an N-terminal domain "homologous to a kringle domain of native human plasminogen" exhibit structural and functional characteristics similar to native kringle domains of plasminogen. Further, the polypeptides referred to herein as having an N-terminal domain "homologous to kringle 1" exhibit characteristics similar to native kringle 1, at least to the extent that the polypeptides can have a higher affinity for ω-aminocarboxylic acids (and functional homologs such as trans-4 aminomethylcyclohexane-1-carboxylic acid, a cyclic acid) than kringle 5. See, e.g., Chang, Y., et al., *Biochemistry* 37: 3258-3271 (1998), incorporated herein by reference, for conditions and protocols for comparison of binding of isolated kringle domain polypeptides to 5-aminopentanoic acid (5-APnA); 6-aminohexanoic acid (6-AHxA), also known as ε-aminocaproic acid (ε-ACA); 7-aminoheptanoic acid (7-AHpA); and trans-4-aminomethylcyclohexane-1-carboxylic acid (t-AMCHA).

References to kringle domains "homologous to kringle 4" are defined similarly, as noted above regarding the phrase "homologous to kringle 1." That is, they exhibit functional characteristics similar to kringle 4 of native human plasminogen as discussed above. These polypeptides also bind immobilized lysine as described above.

The polypeptides of the invention bind immobilized lysine. As used herein, the phrase "binding immobilized lysine" means that the polypeptides so characterized are retarded in their progress relative to mini-plasminogen when subjected to column chromatography using lysine-SEPHAROSE™ as the chromatographic media. Typically, the polypeptides of the invention can be eluted from such chromatographic media (lysine affinity resins) using solutions containing the specific ligand, e.g., ε-ACA, as eluants.

Further, in addition to Chang et al., supra, other references can be consulted by those of skill in the art to determine which residues can be varied by conservative or non-conservative substitution, deletion, or addition to yield a deletion mutant within the scope of the present invention. For example, the following references provide information regarding particular residues of the native kringle domains that may be important for binding of w-aminocarboxylic acids: U.S. Pat. No. 6,538,103 to Ji, et al.; U.S. Pat. No. 6,218,517 to Suzuki; Douglas, J. T., et al., *Biochemistry* 41(10): 3302-10 (2002); Zajicek, J., et al., *J. Mol. Biol.* 301(2): 333-47 (2000); Lee, H., et al., *Arch Biochem Biophys.* 375(2): 359-63 (2000); Castellino, F. and S. McCance, *Ciba Found Symp.* 212: 46-60 (1997); McCance, S., et al., *J. Biol. Chem.* 269: 32405-32410 (1994); Rejante, M. R. and M. Llinas, *Eur. J. Biochem.* 221 (3): 939-49 (1994); Wu, T. P., et al., *Blood Coagul. Fibrinolysis* 5(2): 157-66 (1994); Hoover, C. J., et al., *Biochemistry* 32(41): 10936-43 (1993); Menhart, N., et al., *Biochemistry* 32: 8799-8806 (1993); Thewes, T., et al., J. Biol. Chem., 265 (7): 3906-3915 (1990); Novokhatny, V., et al., *Thromb Res.* 53(3): 243-52 (1989); Motta, A., et al., *Biochemistry* 26(13): 3827-36 (1987); Novokhatny, V., et al., *J. Mol. Biol.* 179: 215-232 (1984); Lerch, P. G., et al., *Eur. J. Biochem.* 107(1): 7-13 (1980); Sottrup-Jensen, L., et al., *Prog. Chem. Fibrinol. Thrombol.* 3: 191-209 (1978); and Wiman, B. and D. Collen, *Nature* 272: 549-545 (1978), all incorporated herein by reference in their entirety.

Because the present inventors have recognized that a valuable, simplified plasmin(ogen) molecule can be prepared having a single N-terminal kringle domain having advantageous functional characteristics (which can be evaluated, in part, by testing for the binding of immobilized lysine as described herein), the present invention can encompass other fibrin-binding domains or regions N-terminal to the activation site. For example, the invention can include polypeptides in which the serine protease domain of plasmin is attached to a fibrin-binding kringle selected from a group including, but not limited to, kringle 4 of human plasminogen, kringle 2 of tPA, or a kringle of apolipoprotein(a). Further, the invention can include polypeptides in which a serine protease domain of plasmin is attached to any other known fibrin-binding modules, such as the "finger" domain of tPA or fibronectin, or the FAB fragment of fibrin-specific IgG.

In some aspects, the polypeptides of the present invention have protein chemical structures (e.g., native-like N-terminus and native-like juncture between the kringle and the serine protease domain) that are identical to the chemical structures found in the naturally occurring forms of human plasma-derived plasmin(ogen). Without being held to a particular theory, it is believed that certain features of a protein can contribute to its immunogenicity, including but not limited to its amino acid sequence. Accordingly, the present invention provides an effective protein therapeutic based on recombinant (TAL6003)-plasminogen by preemptively reducing the potential immunogenicity of (TAL6003)-plasminogen through incorporation of amino acid sequences that resemble native human plasminogen sequences.

In one aspect, the recombinant (TAL6003)-plasminogen polypeptide of the present invention comprises (a) a single N-terminal kringle domain homologous to a kringle domain of native human plasminogen, wherein the last four amino acid residues within the kringle domain are V, P, Q, and C; and (b) a C-terminal domain activation site and serine protease domain homologous to the corresponding domains in human plasminogen; wherein the polypeptide binds to immobilized lysine. In one embodiment, the single N-terminal kringle domain is homologous to kringle 1 or kringle 4 of native human plasminogen. In some embodiments, the immobilized lysine is lysine bound to a solid support matrix selected from the group consisting of lysine-agarose, lysine-hydrogel, and lysine-cross-linked agarose. In another embodiment, the immobilized lysine is lysine-cross-linked agarose.

The recombinant (TAL6003)-plasminogen polypeptides of the present invention can be activated by one of ordinary skill in the art to provide a (TAL6003)-plasmin polypeptide. In one embodiment, the (TAL6003)-plasmin polypeptide exhibits a fibrinolytic activity that is inhibited by α2-antiplasmin at a rate of inhibition that is at least about 5-fold faster than the rate of inhibition of the fibrinolytic activity of mini-plasmin by α2-antiplasmin. In another embodiment, the rate of inhibition is at least about 10-fold, 20-fold, 30-fold, or 40-fold faster than the rate of inhibition of mini-plasmin.

In one embodiment, the recombinant (TAL6003)-plasminogen polypeptide is at least 90% or 95%, or 98% identical to the sequence shown in SEQ ID NO: 2. In another embodiment, the single N-terminal kringle domain is at least 90% identical to the kringle 1 or kringle 4 domain of native human plasminogen; and the C-terminal domain is at least 90% identical to the activation site and serine protease domain of human plasminogen. In some embodiments, the polypeptide has an amino acid sequence as shown in SEQ ID NO: 2, and conservative substitutions thereof. In other embodiments, the polypeptide has an arginine residue at a relative position analogous to that of position 85 of the amino acid sequence shown in SEQ ID NO: 2.

In further embodiments, the single N-terminal kringle domain has at least one residue greater amino acid sequence identity with kringle 1 or kringle 4 of native human plasminogen than with kringle 5 of native human plasminogen, and wherein conservative substitutions of the single N-terminal kringle domain relative to the native sequences of kringles 1 and 4 of human plasminogen are not considered as differing from the native sequences for purposes of the identity comparison with kringle 5. For example, the (TAL6003)-plasminogen described in this invention makes use of amino acid residue modifications to the junction region joining the single kringle domain and the serine protease domain. Accordingly, this juncture between the two domains more closely resembles the naturally occurring juncture between the kringle 5 domain and the serine protease domain of human plasminogen.

In another embodiment, the (TAL6003)-plasminogen described in this invention further comprises a native-like N-terminal sequence. The recombinantly produced (TAL6003)-plasminogen can be cleaved off upon activation to provide recombinant (TAL6003)-plasmin polypeptides also having native-like N-termini.

In particular embodiments, residues at certain positions of the single N-terminal kringle domain of (TAL6003)-plasminogen are conserved relative to kringle 1 of native human plasminogen. These can be residues at positions associated with disulfide bridging and lysine binding, and include Cys84, Cys105, Cys133, Cys145, Cys157, and Cys162, and Pro136-Pro140, Pro143-Tyr146, and Arg153-Tyr156, respectively (positions numbered as shown in FIG. 3). Additionally, particular embodiments of the invention can be characterized chemically by contrast to mini-plasmin(ogen) which has an analogous domain composition (i.e., kringle-serine protease (K-SP) (see Sottrup-Jensen, L., et al., *Progress in Chemical Fibrinolysis and Thrombolysis*, Vol. 3, (Eds: J. F. Davidson, et al.) Raven Press, New York (1978)) but, inter alia, lacks an arginine (Arg) at a relative position analogous to that of position 85 of the amino acid sequence shown in SEQ ID NO: 2. In some embodiments, the (TAL6003)-plasminogen of the invention comprises a single N-terminal kringle domain comprising an Arg residue at a relative position analogous to that of position 85 of the amino acid sequence shown in SEQ ID NO: 2. Non-limiting examples of a relative position analogous to that of position 85 of the amino acid sequence shown in SEQ ID NO: 2 include Arg(153), Arg(234), Arg(324), and Arg(426) positions of the amino acid sequence shown in SEQ ID NO: 4.

In other embodiments, the specific positions of the named residues can vary somewhat while still being present in the polypeptide at structurally and functionally analogous positions (i.e. relative to the kringle structure of the N-terminal domain; see Chang, Y., et al., as discussed above). In some embodiments, the single N-terminal kringle domain of the (TAL6003)-plasmin(ogen) polypeptide has at least one residue greater percent identity with kringle 1 or kringle 4 of native human plasminogen than with kringle 5 of native human plasminogen.

Further, particular embodiments of the invention can be characterized functionally by contrast to mini-plasmin (ogen). In preferred embodiments, the (TAL6003)-plasmin of the invention exhibits an increased rate of inhibition by α2-antiplasmin, e.g., as much as about one or two orders of magnitude faster than the rate of inhibition of mini-plasmin. Further, in particular embodiments, (TAL6003)-plasmin binds immobilized lysine (e.g., lysine-SEPHAROSE™)

Characterization of the single N-terminal kringle domain of (TAL6003)-plasminogen as "N-terminal" means only that the domain is present N-terminal to the activation site and does not mean that additional amino acids residues N-terminal to the domain itself are not present. Further, the number and identity of residues interposed between the most C-terminal cysteine residue of the single N-terminal kringle domain (i.e., the most C-terminal Cys residue shown in FIG. 4) and the activation site of plasminogen can be varied without departing from the scope of the present invention. One of skill in the art will be able to determine these variations that achieve the benefits of the invention (kringle 1-like binding of w aminocarboxylic acids, without substantial increase in size of the deletion mutant or introduction of potentially problematic glycosylation sites) without undue experimentation based on the disclosure herein and the references cited herein for guidance regarding kringle 1 function and structure.

Accordingly, the invention relates to polynucleotides, polypeptides, recombinant methods for producing the polypeptides, vectors containing the polynucleotides, expression systems for producing the polypeptides, and cultured host cells comprising such expression systems.

As noted, in one aspect, the invention relates to a polynucleotide encoding the polypeptide disclosed herein or a polypeptide having conservative amino acid substitutions thereof. Guidance regarding selection of "conservative" amino acid substitutions is provided in more detail below. In one embodiment, the polynucleotide is DNA.

In another aspect, the invention relates to a method of making a vector comprising inserting the polynucleotide of the invention into a vector. In another aspect, the invention relates to a vector produced by the method of the invention.

In another aspect, the invention relates to a method of making a cultured host cell comprising introducing the vector of the invention into a cultured host cell. In another aspect, the invention relates to a cultured host cell produced by the method of the invention.

In another aspect, the invention relates to an isolated polypeptide of the invention, produced by a method comprising: (a) introducing a vector comprising a polynucleotide encoding the polypeptide into a cultured host cell; (b) culturing the host cell; and (c) recovering the polypeptide. In another aspect, the invention relates to a method for producing a polypeptide comprising: (a) culturing the host cell of the invention under conditions that the vector is expressed; and (b) recovering the polypeptide.

In another aspect, the invention relates to cells containing at least one polynucleotide of the invention.

In one embodiment, the polynucleotide comprises the nucleotide sequence as shown in SEQ ID NO: 1. In another embodiment, the polynucleotide comprises nucleotides 4 through 1032 of the nucleotide sequence shown in SEQ ID NO: 1. In other embodiments, the polypeptide comprises the amino acid sequence as shown in SEQ ID NO: 2.

Polynucleotides

The polynucleotides of the invention include variants that have substitutions, deletions, and/or additions that can involve one or more nucleotides. The variants can be altered in coding regions, non-coding regions, or both. Alterations in the coding regions can produce conservative or non-conservative amino acid substitutions, deletions, or additions. Especially preferred among these are silent substitutions, additions and deletions, which do not alter the properties and activities of the (TAL6003)-plasmin(ogen) protein or portions thereof. Also especially preferred in this regard are conservative substitutions (see below).

Further embodiments of the invention include nucleic acid molecules comprising a polynucleotide having a nucleotide sequence at least 90% identical, and more preferably at least 95%, 96%, 97%, 98% or 99% identical to (a) a nucleotide sequence encoding a polypeptide having the complete amino acid sequence in SEQ ID NO: 2; (b) a nucleotide sequence encoding a polypeptide having the amino acid sequence in SEQ ID NO: 2; and (c) a nucleotide sequence complementary to any of the nucleotide sequences in (a) or (b) above.

In one embodiment, the nucleic acid molecule of the present invention comprises a polynucleotide having a nucleotide sequence that encodes a polypeptide having the amino acid sequence shown in SEQ ID NO: 2. In other embodiments, the nucleic acid molecule comprises a polynucleotide having the nucleotide sequence shown in SEQ ID NO: 1, or a degenerate variant thereof.

By a polynucleotide having a nucleotide sequence at least, for example, 95% "identical" to a reference nucleotide sequence encoding a (TAL6003)-plasminogen is intended that the nucleotide sequence of the polynucleotide be identical to the reference sequence except that the polynucleotide sequence can include up to five point mutations per each 100 nucleotides of the reference nucleotide sequence encoding the (TAL6003)-plasminogen polypeptide. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5'- or 3'-terminal positions of the reference nucleotide sequence or anywhere between those terminal positions, interspersed either individually among nucleotides in the reference sequence or in one or more contiguous groups within the reference sequence.

As noted above, two or more polynucleotide sequences can be compared by determining their percent identity. Two or more amino acid sequences likewise can be compared by determining their percent identity. The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, *Advances in Applied Mathematics* 2: 4 82-489 (1981). This algorithm can be extended to use with peptide sequences using the scoring matrix developed by Dayhoff, *Atlas of Protein Sequences and Structure*, M. O. Dayhoff ed., 5 suppl. 3: 353-358, National Biomedical Research Foundation, Washington, D.C., USA, and normalized by Gribskov, *Nucl. Acids Res.* 14(6): 6745-6763 (1986). An implementation of this algorithm for nucleic acid and peptide sequences is provided by the Genetics Computer Group (Madison, Wis.) in their BESTFIT utility application. The default parameters for this method are described in the Wisconsin Sequence Analysis Package Program Manual, Version 8 (1995) (available from Genetics Computer Group, Madison, Wis.).

For example, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence shown in SEQ ID NO: 1 will encode a (TAL6003)-plasminogen polypeptide. In fact, because degenerate variants of these nucleotide sequences all encode the same polypeptide, this will be clear to the skilled artisan even without performing any functional assays or measurements described herein. It will be further recognized in the art that, for such nucleic acid molecules that are not degenerate variants, a reasonable number will also encode a polypeptide having (TAL6003)-plasminogen polypeptide activity. This is because the skilled artisan is fully aware of amino acid substitutions that are either less likely or not likely to significantly affect protein function (e.g., replacing one aliphatic amino acid with a second aliphatic amino acid).

Recently, advances in the synthetic production of longer polynucleotide sequences have enabled the synthetic production of nucleic acids encoding significantly longer polypeptides without the use of traditional cloning techniques. Commercial providers of such services include Blue Heron, Inc., Bothell, Wash. Technology utilized by Blue Heron, Inc. is described in U.S. Pat. Nos. 6,664,112; 6,623,928; 6,613,508; 6,444,422; 6,312,893; 4,652,639; U.S. Published Patent Application Nos. 2002/0119456A1; 2002/0077471A1; and Published International Patent Applications (Publications Nos) WO 03054232A3; WO 0194366A1; WO 9727331A2; and WO 9905322A1, all incorporated herein by reference.

Of course, traditional techniques of molecular biology, microbiology, and recombinant nucleic acid can also be used to produce the polynucleotides of the invention. These techniques are well known and are explained in, for example, *Current Protocols in Molecular Biology*, F. M. Ausebel, ed., Vols. I, II, and III (1997); Sambrook et al., *Molecular Cloning: A Laboratory Manual,* 2nd Edition, Cold Spring Harbor Laboratory Press, Cold Spring Harbor, N.Y. (1989); DNA *Cloning: A Practical Approach*, D. N. Glover, ed., Vols. I and II (1985); *Oligonucleotide Synthesis*, M. L. Gait, ed. (1984); *Nucleic Acid Hybridization*, Hames and Higgins, eds. (1985); *Transcription and Translation*, Hames and Higgins, eds. (1984); *Animal Cell Culture*, R. I. Freshney, ed. (1986); Immobilized Cells and Enzymes, IRL Press (1986); Perbal, "*A Practical Guide to Molecular Cloning*"; the series, *Methods in Enzymology*, Academic Press, Inc. (1984); *Gene Transfer Vectors for Mammalian Cells*, J. H. Miller and M. P. Calos, eds., Cold Spring Harbor Laboratory (1987); and *Methods in Enzymology*, Wu and Grossman and Wu, eds., respectively, Vols. 154 and 155, all incorporated herein by reference.

Vectors and Cultured Host Cells

The present invention also relates to vectors which include the isolated nucleic acid molecules of the present invention, cultured host cells which are genetically engineered with the recombinant vectors, and the production of the (TAL6003)-plasmin(ogen) polypeptides by recombinant techniques.

Recombinant constructs can be introduced into cultured host cells using well-known techniques such as infection, transduction, transfection, transvection, electroporation, and transformation. The vector can be, for example, a phage, plasmid, viral or retroviral vector. Retroviral vectors can be replication competent or replication defective. In the latter case, viral propagation generally will occur only in complementing cultured host cells.

The polynucleotides can be joined to a vector containing a selectable marker for propagation in a cultured host. Generally, a plasmid vector is introduced in a precipitate, such as a calcium phosphate precipitate, or in a complex with a charged lipid. If the vector is a virus, it can be packaged in vitro using an appropriate packaging cell line and then transduced into cultured host cells.

Preferred are vectors comprising cis-acting control regions to the polynucleotide of interest. Appropriate trans-acting factors can be supplied by the cultured host, supplied by a complementing vector, or supplied by the vector itself upon introduction into the cultured host.

In certain embodiments in this regard, the vectors provide for specific expression, which can be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

DNA inserts should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs can include a translation initiating at the beginning and a termination codon (UAA, UGA, or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate cultured hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described cultured host cells are known in the art.

Among vectors preferred for use in bacteria include e.g., pET24b or pET22b available from Novagen, Madison, WI (pET-24b(+) and pET-22b(+)=pET Expression System 24b (Cat. No. 69750) and 22b (Cat. No. 70765), respectively, EMD Biosciences, Inc., Novagen Brand, Madison, Wis.; see product information section regarding pET-24b and pET-22b for details regarding vector), pQE70, pQE60 and pQE-9, available from Qiagen Inc., Valencia, Calif.; pBS vectors, PHAGESCRIPT vectors, BLUESCRIPT vectors, pNH8A, pNH16a, pNH18A, pNH46A, available from Stratagene, LaJolla, Calif.; and ptrc99a, pKK223-3, pKK233-3, pDR540, pRIT5 available from Pharmacia (now Pfizer, Inc., New York, N.Y.). Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Bacterial promoters suitable for use in the present invention include the *E. coli* lacI and lacZ promoters, the T3 and T7 promoters, the gpt promoter, the lambda PR and PL promoters, and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of a vector construct into the cultured host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., *Basic Methods In Molecular Biology*, 2nd Edition (1995).

Transcription of the DNA encoding the polypeptides of the present invention by higher eukaryotes can be increased by inserting an enhancer sequence into the vector. Enhancers are cis-acting elements of DNA, usually about from 10 to 300 by that act to increase transcriptional activity of a promoter in a given cultured host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals can be incorporated into the expressed polypeptide. The signals can be endogenous to the polypeptide or they can be heterologous signals.

The polypeptide can be expressed in a modified form, such as a fusion protein, and can include not only secretion signals, but also additional heterologous functional regions. For instance, a region of additional amino acids, particularly charged amino acids, can be added to the N-terminus, for example, the polypeptide to improve stability and persistence in the cultured host cell, during purification, or during subsequent handling and storage. Also, peptide moieties can be added to the polypeptide to facilitate purification. Such regions can be removed prior to final preparation of the polypeptide. The additions of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP 0 464 533 A1 (Canadian counterpart, 2,045,869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties. On the other hand, for some uses it would be desirable to be able to delete the Fc part after the fusion protein has been expressed, detected, and purified in the advantageous manner described. This is the case when Fc portion proves to be a hindrance to use in therapy and diagnosis, for example, when the fusion protein is to be used as antigen for immunizations. In drug discovery for example, human proteins have been fused with Fc portions for the purpose of high-throughput screening assays (such as hIL5-receptor, to identify antagonists of hIL-5). See, Bennett, D., et al., *J. Molecular Recognition*, 8: 52-58 (1995) and Johanson, K. et al., *J. Biol. Chem.* 270(16): 9459-9471 (1995).

(TAL6003)-plasminogen can be recovered and purified from recombinant cell cultures by well-known methods including those specifically described in the examples herein. Polypeptides of the present invention include naturally purified products, products of chemical synthetic procedures, and products produced by recombinant techniques from a prokaryotic or eukaryotic cultured host, including, for example, bacterial, yeast, higher plant, insect and mammalian cells. In addition, polypeptides of the invention can also include an initial modified methionine residue, in some cases as a result of host-mediated processes.

Polypeptides

The polynucleotides of the invention include those encoding variations and particular examples of the polypeptides of the invention. For example, guidance concerning how to make phenotypically silent amino acid substitutions is provided in Bowie, J. U. et al., "Deciphering the Message in Protein Sequences: Tolerance to Amino Acid Substitutions," *Science* 247: 1306-1310 (1990), wherein the authors indicate that proteins are surprisingly tolerant of amino acid substitutions. Although any number of substitutions within the scope of the invention can be obtained by application of such general principles, for specific guidance regarding substitutions, the references cited herein regarding structure and function of kringle 1 domains can be consulted by one of skill in the art.

It will further be appreciated that, depending on the criteria used, the exact "position" or sequence of the kringle, activation site, and serine protease domains of the (TAL6003)-plasminogen can differ slightly in particular variations within the scope of the present invention. For example, the exact location of the kringle domain relative to the activation site can vary slightly and/or the sequence N-terminal to the kringle domain can vary in length. Thus, the invention includes such variations of the (TAL6003)-plasminogen polypeptides which exhibit (TAL6003)-plasminogen polypeptide activity as disclosed herein. Such variants include deletions, insertions, inversions, repeats, and substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247: 1306-1310 (1990).

Thus, fragments, derivatives or analogs of the polypeptide of SEQ ID NO: 2 can be (i) ones in which one or more of the amino acid residues (e.g., 3, 5, 8, 10, 15 or 20 residues) are substituted with a conserved or non-conserved amino acid residue (preferably a conserved amino acid residue). Such substituted amino acid residues may or may not be one encoded by the genetic code, or (ii) ones in which one or more of the amino acid residues includes a substituent group (e.g., 3, 5, 8, 10, 15 or 20), or (iii) ones in which the mature polypeptide is fused with another compound, such as a compound to increase the half-life of the polypeptide (for example, polyethylene glycol), or (iv) ones in which the additional amino acids are fused to the mature polypeptide, such as an IgG Fc fusion region peptide or leader or secretory sequence or a sequence which is employed for purification of the mature polypeptide or a proprotein sequence. Such fragments, derivatives, and analogs are deemed to be within the scope of those skilled in the art from the teachings herein.

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given (TAL6003)-plasminogen polypeptide will not be more than 50, 40, 30, 25, 20, 15, 10, 5 or 3.

Amino acids in the (TAL6003)-plasminogen of the present invention that are essential for function can be identified by methods known in the art, such as site-directed mutagenesis or alanine-scanning mutagenesis (Cunningham and Wells, *Science* 244: 1081-1085 (1989)). The latter procedure introduces single alanine mutations at every residue in the molecule. The resulting mutant molecules are then tested for biological activity, e.g., as shown in the examples provided herein. Sites that are critical for ligand binding can also be determined by structural analysis such as crystallization, nuclear magnetic resonance, or photoaffinity labeling (Smith, et al., *J. Mol. Biol.* 224: 399-904 (1992) and de Vos, et al. *Science* 255: 306-312 (1992)). Even if deletion of one or more amino acids from the N-terminus of a protein results in modification or loss of one or more biological functions of the protein, other biological activities can be retained.

It is also contemplated that polypeptides useful in production of the "isolated polypeptides" of the invention can produced by solid phase synthetic methods. See Houghten, R. A., *Proc. Natl. Acad. Sci. USA* 82: 5131-5135 (1985); and U.S. Pat. No. 4,631,211 to Houghten et al. (1986).

The polypeptides of the present invention can be provided in an isolated form. By "isolated polypeptide" is intended a polypeptide removed from its native environment. Thus, a polypeptide produced and/or contained within a recombinant cultured host cell is considered isolated for purposes of the present invention. Also intended, as "isolated polypeptides" are polypeptides that have been purified, partially or substantially, from a recombinant cultured host.

Polypeptides having an amino acid sequence of an indicated percent identity to a reference amino acid sequence of a (TAL6003)-plasminogen polypeptide can be determined using the methods, including computer-assisted methods, indicated above regarding polynucleotides. Polypeptide amino acid sequences are examined and compared just as are the nucleotide sequences in the foregoing discussion. One of skill in the art will recognize that such concepts as the molecular endpoints discussed for polynucleotides will have direct analogs when considering the corresponding use of such methods and programs for polypeptide analysis. For example, the manual corrections discussed regarding polynucleotides refer to 5'- and 3'-endpoints of nucleic acids, but the same discussion will be recognized as applicable to N-termini and C-termini of polypeptides.

The invention encompasses (TAL6003)-plasminogen polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications can be carried out by known techniques, including but not limited, to specific chemical cleavage by cyanogen bromide, trypsin, chymotrypsin, papain, *S. aureus* V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition of an N-terminal methionine residue as a result of vectors and constructs adapted for expression of (TAL6003)-plasminogen polypeptides in prokaryotic cultured host cells. The polypeptides can also be modified with a detectable label, such as an enzymatic, fluorescent, isotopic, or affinity label to allow for detection and isolation of the protein.

Pharmaceutical Compositions and Methods of Treatment (TAL6003)-plasmin(ogen) can be formulated for therapeutic use in accordance with the methods and compositions described in U.S. patent application Ser. No. 10/143,112; and Novokhatny, V., et al., *J. Thromb. Haemost.* 1(5): 1034-41 (2003), both incorporated herein by reference. For example, a low-pH (from about 2.5 to about 4), low-buffering capacity buffer can be used for formulation of (TAL6003)-plasmin. Additionally, other methods and formulations known to those of skill in the art, as practiced with plasmin, mini-plasmin, and/or micro-plasmin, can be used to formulate the (TAL6003)-plasmin of the invention for therapeutic administration.

The (TAL6003)-plasmin(ogen) can be used to treat a variety of thrombotic diseases or conditions, for example, according to the methods as described in U.S. Pat. Nos. 6,355,243, 6,964,764, and 6,969,515, all incorporated herein by reference. Again, as with the possible pharmaceutical formulations applicable to (TAL6003)-plasmin, (TAL6003)-plasmin can also be administered therapeutically by methods known in the art, for example, those that may be currently practiced with plasmin, mini-plasmin, and/or micro-plasmin.

EXAMPLES

Expression Vector Design

The amino acid sequence for (TAL6003)-plasminogen is shown in SEQ ID NO: 2. A polynucleotide having the nucleotide sequence encoding (TAL6003)-plasminogen was codon-optimized for *E. coli* expression and mRNA stability to provide the DNA sequence as shown in SEQ ID NO: 1. This polynucleotide was cloned into the NdeI and BamH1 sites of *E. coli* expression vector pET24b(+) (Novagen; Madison, Wis.) to produce cytosolic protein.

As illustrated in Table 1, expression in bacteria (e.g., *E. coli*) provided a recombinant (TAL6003)-plasminogen polypeptide having the amino acid sequence as shown in SEQ ID NO: 2 (i.e., a recombinant (TAL6003)-plasminogen with an N-terminal methionine (i.e., M1) immediately preceding the arginine amino acid residue (i.e., R2) corresponding to the arginine at position 70 (i.e., R70) of the native human plasminogen amino acid sequence shown in SEQ ID NO: 4 (see also, e.g., FIG. 3). Such a recombinant product was susceptible to further cleavage to yield additional proteins having different N-termini including a protein with an N-terminal lysine (i.e., K10) or valine (i.e., V11) corresponding, respectively, to the lysine at position 78 (i.e., K78) or the valine at position 79 (i.e., V79) of native human plasminogen.

thiogalactopyranoside) was analyzed by SDS-PAGE. Expression estimates were at least about 250 mg/L cell culture in shaker flasks.

Cell type BL21(DE3) RIL is engineered to express rare *E. coli* tRNAs coding for Arg, Ile, and Leu. Further, both BL21 (DE3) and BLR(DE3) are B strain *E. coli* that is classified as non-pathogenic to humans and animals based on the absence of virulence and colonization factors. BLR(DE3) cells lack the recA gene for DNA recombination, and induction of lamba phage has not been reported with these cells. A research cell bank of the (TAL6003)-plasminogen construct in BLR(DE3) cells was produced and tested for purity, identity, and induction of bacteriophage at Charles River Laboratories (Malvern, Pa.). The testing confirmed the identity and purity of the research cell bank and the cells passed the phage induction test with no phage observed (data not shown).

Production of (TAL6003)-plasminogen (i.e., based on SEQ ID NO: 2) was confirmed in larger scale expression in which cells were lysed and both soluble protein and purified inclusion bodies were examined by SDS-PAGE.

The following typical protocol has been used for expression of (TAL6003)-plasminogen:

A single colony of *E. coli* cells (e.g., BL21(DE3) RIL, BL21(DE3), or BLR(DE3) containing the (TAL6003)-plasminogen vector was used to inoculate 5 mL of LB/kanamycin

TABLE 1

N-termini of native plasmin(ogen) (e.g., based on SEQ ID NO: 4) and (TAL6003)-plasmin(ogen) (e.g., based on SEQ ID NO: 2, or a variant thereof)

Native Plasminogen comprising 19 amino acid leader sequence (e.g., based on SEQ ID NO: 4):

$M^{-19}EHKE \ldots E^{01}PLDDY \ldots M^{69}R^{70}DVVLFEKK^{78}V^{79}YLSEC$

Native "Lys-Plasminogen" (i.e., cleavage of leader sequence):

$E^{01}PLDDY \ldots M^{69}R^{70}DVVLFEKK^{78}V^{79}YLSEC \ldots$
(see SEQ ID NO: 15)

Native Plasmin species possible based on cleavage, if any, of Lys-Plasminogen:

(see SEQ ID NO: 14) $M^{69}R^{70}DVVLFEKK^{78}V^{79}YLSEC \ldots$
(see SEQ ID NO: 13)    $K^{78}V^{79}YLSEC \ldots$
(see SEQ ID NO: 12)         $V^{79}YLSEC \ldots$ Recombinant (TAL6003)-plasminogen polypeptides of the present invention:

(e.g., based on SEQ ID NO: 2) $M^{01}R^{02}DVVLFEKK^{10}V^{11}YLSEC \ldots$

Additional proteins based on further cleavage of a (TAL6003)-plasminogen (e.g., based on SEQ ID NO: 2):

(see SEQ ID NO: 11) $K^{10}V^{11}YLSEC \ldots$
(SEQ ID NO: 5) $V^{11}YLSEC \ldots$ ↓ indicates potential cleavage sites.

(TAL6003)-Plasminogen Expression and Purification

The expression vector comprising the DNA encoding (TAL6003)-plasminogen was transformed into a variety of cells including BL21(DE3) RIL (Stratagene, La Jolla, Calif.), BL21(DE3) (genotype: F⁻ompT hsdSB (rB⁻ mB⁻) gal dcm (DE3)) (EMB Biosciences, Inc., San Diego, Calif.), and BLR (DE3) (genotype: F⁻ompT hsdSB (rB⁻ mB⁻) gal dcm (DE3) Δ(srl⁻ recA)306::Tn10(TetR)), and protein over-expression following induction by 1 mM IPTG (isopropyl-beta-D-

(30 μg/mL) and was incubated for 8 hours at 37° C. on a shaker. After that, a 50 μL-aliquot was taken form the cultured bacterial suspension for further growth in fresh media. The procedure was repeated after 16 hours with 6 mL of bacterial culture and 250 mL of the media. Cultures were grown at 37° C. with shaking to an OD600 nm of ~1.0, and IPTG was added to 1 mM final concentration. Cultures were grown for an additional 5 hours. Cells were harvested by centrifugation at 5,000×g and cell pellets were dissolved in 20 mM Tris pH 8.0 containing 20 mM EDTA and frozen at −80° C.

To purify (TAL6003)-plasminogen, cell pellets were thawed and buffer added until the solution volume was approximately 1/20th that of the original cell culture volume. After that, lysozyme was added to a final concentration of 0.5 mg/mL and the cells were stirred rapidly at 4° C. for 10-15 minute. Then, Triton X-100 was added to 1% final concentration and stirring continued for another 10 min. DNAse I (0.05 mg/mL) and $MgCl_2$ (2.5 mM) were added and stirring was continued at 4° C. for 30 minutes or until the solution was no longer viscous. The final solution was centrifuged at 4° C. for 30 min at 15,000×g and the supernatant was discarded.

The cell pellet was washed three times with wash solution (50 mM Tris-HCl, pH 7.4 containing 10 mM EDTA, 1% Triton-X-100, and 0.5 M urea), and the final pellet was dissolved in 40 mL of extraction buffer (PBS, pH 7.4 containing 10 mM EDTA, 20 mM DTT, and 6 M guanidine-HCl) and stored at 4° C. overnight. After 16 hours, the solution was centrifuged for 30 minutes at 15,000×g to remove solids and the supernatant was slowly added to the refolding solution (50 mM Tris-HCl, pH 8.3, 3.5 M guanidine-HCl, 0.5 M arginine-HCl, 10 mM EDTA, 3 mM GSH, 0.3 mM GSSG) while stifling at 4° C. The refolding procedure was carried out at protein concentration of about 0.29 g/L.

The refolding solution was kept for 2 days at 4° C. undisturbed and then dialyzed against an 8-fold volume of 0.1 M Tris-HCl pH 8.0 containing 10 mM EDTA, 0.15 M NaCl, 0.15 M arginine-HCl, over a period of 8-10 hours with frequent changes of the buffer solution.

The protein solution was then removed from dialysis and concentrated using AMICON filters with the membrane cut-off of 10 kDa to approximately 10-20 mL and dialyzed overnight versus a 100-fold volume of 0.1 M Tris pH 8.0 containing 10 mM EDTA, 0.15 M NaCl. This material was centrifuged to remove particulates, and then passed over lysine affinity resin (Lysine-SEPHAROSE™ 4B; Amersham Biosciences, Piscataway, N.J.). (TAL6003)-plasminogen was eluted from the resin using Tris-buffered saline, pH 8.0 containing 0.2 M epsilon aminocaproic acid ($\epsilon$-ACA).

Typically, 80 mg of inclusion bodies could be isolated from 1 liter of cell culture and 40 mg could be eluted in the lysine-SEPHAROSE chromatography step.

Properties of (TAL6003)-Plasminogen

Purified (TAL6003)-plasminogen appeared as a band in the 35-40 kDa region by SDS-PAGE analysis of reduced (dithiothreitol-treated) and non-reduced protein. Its molecular mass, determined by MALDI mass-spectrometry, was about 38,140 Da, which is close to the expected value.

Figure 6:
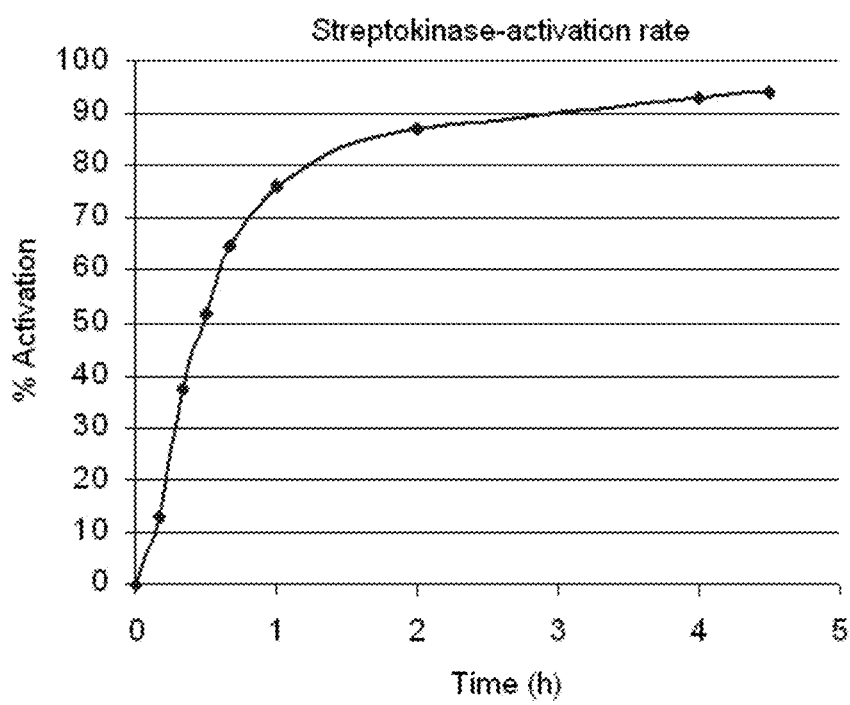
FIG. 6 is a graphic representation of activation of (TAL6003)-plasminogen by streptokinase.

To determine the rate of activation of (TAL6003)-plasminogen by streptokinase, 1 mg/mL of recombinant (TAL6003)-plasminogen was mixed with streptokinase at a 1:100 (TAL6003)-plasminogen to streptokinase ratio and incubated at room temperature at pH 7. At various time points, samples were removed and quenched with SDS-Page buffer and analyzed on reduced SDS-PAGE followed by densitometry to determine the conversion of the one-chain (TAL6003)-plasminogen molecule into a two-chain (TAL6003)-plasmin. Percent activation of (TAL6003)-plasminogen by streptokinase is shown in FIG. 6 as loss of full-length (TAL6003)-plasminogen over time as determined by SDS-PAGE.

Figure 7:
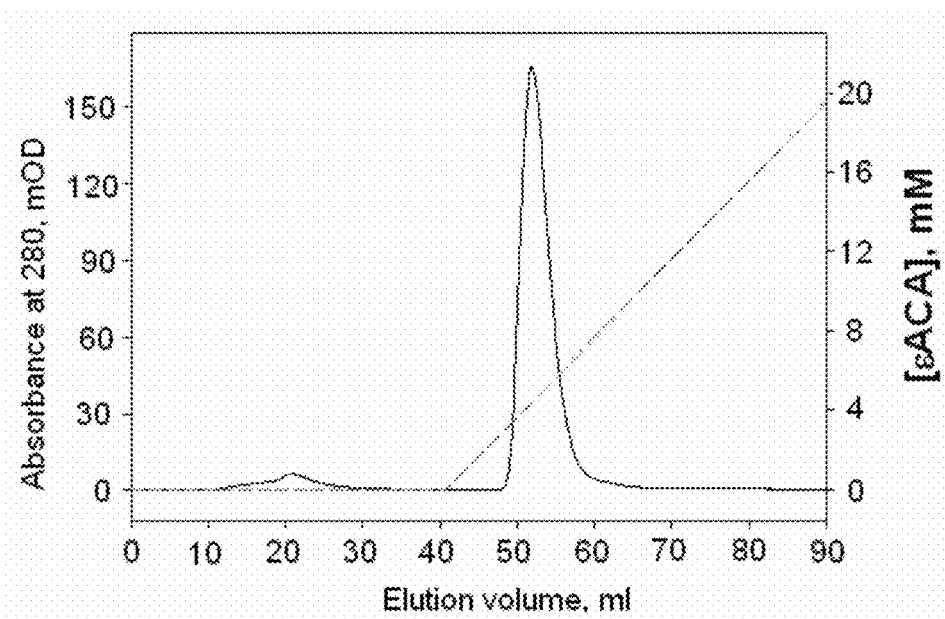
FIG. 7 is a chromatogram showing binding of (TAL6003)-plasminogen to lysine-SEPHAROSE™ 4B: 0.5 mg of purified (TAL6003)-plasminogen was applied on the lysine-SEPHAROSE™ 4B column (1×3 cm) equilibrated with Tris-buffered saline, pH 7.4. Bound protein was eluted from the column by a 0-20 mM gradient of ε-aminocaproic acid (ε-ACA) as a single peak. The absorbance at 280 nm and the concentration of ε-ACA, as a function of the effluent volume are presented on the graph.

To confirm the functionality of kringle 1, we determined the binding of TAL6003-plasminogen to lysine-SEPHAROSE™ 4B. As shown in FIG. 7, (TAL6003)-plasminogen bound to lysine-SEPHAROSE™ and could be eluted from the column by a 0-20 mM $\epsilon$-ACA gradient as a single peak at about 4 mM. The ability of refolded (TAL6003)-plasminogen to bind lysine-SEPHAROSE™ indicates that the kringle domain of the molecule is properly folded and the lysine-binding site is fully active.

To further confirm the functionality of kringle 1, the binding of $\epsilon$-ACA to (TAL6003)-plasminogen was measured by monitoring the associated changes in protein fluorescence as described by Matsuka et al., *Eur. J. Biochem.* 190: 93-97 (1990) and Douglas et al., *J. Biochemistry* 41: 3302-3310 (2002), all incorporated herein by reference. Binding of $\epsilon$-ACA to kringle 1 of (TAL6003)-plasminogen results in a decrease in fluorescence, likely due to quenching of the tryptophan residues which are part of the lysine-binding site.

To monitor this process, 4 µL to 16 µL aliquots of a concentrated solution of $\epsilon$-ACA were added to 2 mL of 5 µM (TAL6003)-plasminogen in 50 mM Tris buffer containing 20 mM NaCl, pH 8.0, 25° C. The fluorescence was monitored at an excitation wavelength of 298 nm and an emission wavelength of 340 nm in a FLUOROMAX fluorescence spectrophotometer (Jobin Yvon, Inc., Edison, N.J.); after each addition of $\epsilon$-ACA, the solution was allowed to equilibrate until no further changes in fluorescence were observed.

The resulting fluorescence values were corrected for dilution and plotted versus the concentration of $\epsilon$-ACA over a range of 0-50 µM $\epsilon$-ACA. Data were fitted by non-linear regression to obtain a $K_d$ of about 19 µM.

One property of plasminogen is its ability to bind fibrin. In order to determine whether (TAL6003)-plasminogen retains the ability to interact with fibrin, its fibrin-binding properties was tested in a microtiter plate assay in which binding of (TAL6003)-plasminogen to fibrin was assessed by its subsequent activation by tPA and resulting clot lysis. For this purpose, 100 µL of 5 mg/mL fibrinogen was polymerized with thrombin in each well of a microtiter plate. Various concentrations of (TAL6003)-plasminogen was added on top of the fibrin clots and incubated for 1 hour at 37° C. The plate was washed extensively with PBS while the fibrin clots are still intact and attached to the wells. After washing, a 0.1 mg/mL solution of tPA was added to each well and the plate was incubated 2 hours at 37° C. As a result, some of the clots were completely dissolved and some were partially dissolved, while wells with very low amounts of (TAL6003)-plasminogen and control wells remained practically intact. The degree of fibrinolysis was monitored by measuring the 280 nm absorbance of remainders of the initial clots reconstituted in 1 M NaOH. The absorbance values were plotted as a function of (TAL6003)-plasminogen concentration.

Figure 8:
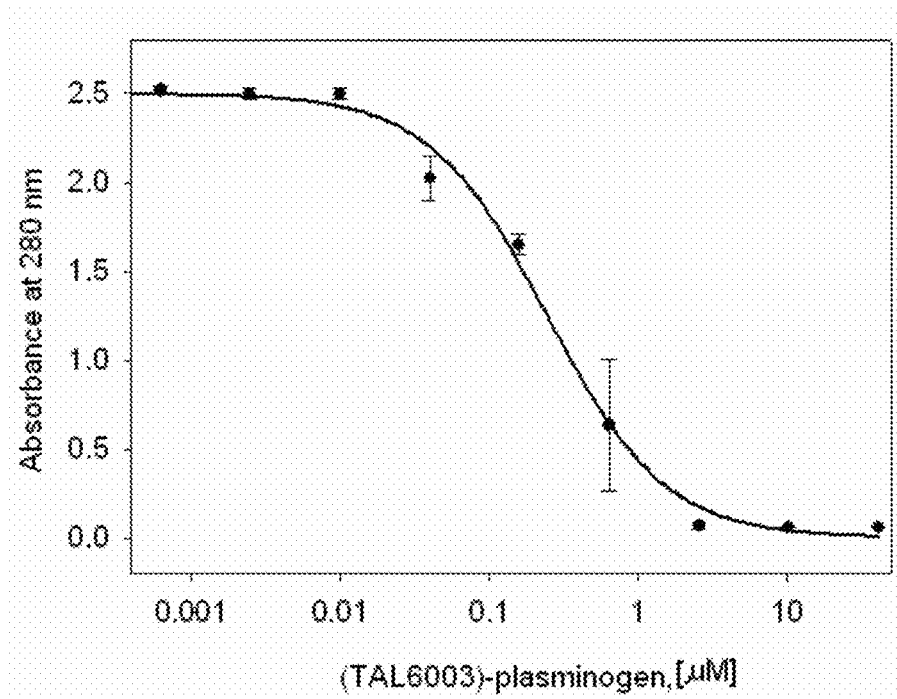
FIG. 8 shows binding of (TAL6003)-plasminogen to fibrin as assessed by its subsequent activation by tPA and resulting clot lysis.

As shown in FIG. 8, the binding of (TAL6003)-plasminogen to fibrin followed a classic, sigmoidal binding curve. Using this assay, it was found that (TAL6003)-plasminogen binds fibrin with affinity comparable to that of full-length plasminogen and the $C_{50}$ of this interaction (~0.3 µM) is comparable to the $K_d$ of fibrin-binding of full-length plasminogen.

These experiments indicate that (TAL6003)-plasminogen can bind fibrin. Further, at least the interaction of (TAL6003)-plasminogen with lysine-Sepharose, its ability to bind $\epsilon$-ACA with the expected $K_d$, its ability to bind fibrin, and its ability to be activated by a plasminogen activator all indicated that this molecule was produced in the *E. coli* system in a fully functional form.

(TAL6003)-Plasmin Purification and Formulation

The addition of SK to the purified (TAL6003)-plasminogen solution effects the conversion of (TAL6003)-plasminogen to (TAL6003)-plasmin. The protein was concentrated to 2 mg/mL and diluted 1:1 with 50% glycerol to produce a 1 mg/mL solution in 25% glycerol. The solution was brought to room temperature and streptokinase was added at a 1:100 molar ratio of SK:(TAL6003)-plasminogen. The reaction was incubated without stifling at room temperature for 4.5 hrs. The reaction was then slowed down by addition of NaCl to a 0.5 M final concentration. Analysis of activation by SDS-PAGE indicated a 90% yield of activated protein.

Activated (TAL6003)-plasmin was purified by Benzamidine Affinity Chromatography. The purpose of benzamidine affinity purification was the separation of unactivated (TAL6003)-plasminogen and impurities, including (TAL6003)-plasmin degradation products, from active (TAL6003)-plasmin. The SK activation solution was applied to an equilibrated Benzamidine-SEPHAROSE™ 4 Fast Flow column. The (TAL6003)-plasmin, both clipped and intact, was captured by the affinity resin while the aforementioned impurities flowed through the column. The column was washed with the equilibration buffer until the absorbance at 280 nm reached baseline. The bound (TAL6003)-plasmin was then eluted using a low pH ε-ACA step to strip all remaining protein from the column. Typical yields were 75%, with protein that is 95% active as measured by chromogenic plasmin potency assay.

Because (TAL6003)-plasmin, similar to full-length plasmin, is prone to auto-degradation at physiological pH, pH 3.6 was chosen for the final formulation (acidified with acetic acid-saline). As shown previously for plasmin by Novokhatny et al., *J. Thromb. Haemost.* 1(5): 1034-41 (2003), incorporated by reference, and confirmed in experiments with (TAL6003)-plasmin, this low buffering-capacity, low pH formulation not only allows safe storage of active plasmins for prolonged periods of time, but is also compatible with parenteral administration of these direct thrombolytics. When mixed with plasma or neutral pH buffers, (TAL6003)-plasmin is quickly re-activated.

Enzymatic Properties of (TAL6003)-Plasmin

The amidolytic activity of (TAL6003)-plasmin was examined using the plasmin substrate D-Val-Leu-Lys-p-nitroanilide (S-2251) (DiaPharma, West Chester, Ohio).

For (TAL6003)-plasmin, at pH 7.4, 25° C. in PBS buffer, the Michaelis-Menten constant ($K_M$) for S-2251 was found to also be 141 µM (Table 2). The $k_{cat}$ for the preparation was found to be about 725 min-1. Using 4-nitrophenyl 4-guanidinobenzoate hydrochloride (pNPGB) titration (Chase, T. and E. Shaw, *Methods Enzymol.* 197: 20-27 (1970)), the percent of functional active sites was found to be 67%. Correcting $k_{cat}$ for percent active sites, a $k_{cat}$ of about 725 min$^{-1}$ was determined. This value was very close to the value determined in the same assay for full-length plasmin, 820±23 min$^{-1}$ and for micro-plasmin (lacking all five kringles), 795±24 min$^{-1}$. These data indicate that presence or absence of kringles does not affect the catalytic activity of the serine protease domain.

TABLE 2

Steady-state kinetic parameters for various plasmin species with substrate S-2251, in PBS buffer, pH 7.4, 25° C.

| | $K_m$ | $k_{cat}$ |
|---|---|---|
| plasmin | 220 ± 9 µM | 820 ± 23 min$^{-1}$ |
| mini-plasmin | 160 ± 30 µM | 770 ± 70 min$^{-1}$ |

TABLE 2-continued

Steady-state kinetic parameters for various plasmin species with substrate S-2251, in PBS buffer, pH 7.4, 25° C.

| | $K_m$ | $k_{cat}$ |
|---|---|---|
| micro-plasmin | 145 ± 13 µM | 795 ± 24 min$^{-1}$ |
| (TAL6003)-plasmin | 141 ± 9 µM | 725 min$^{-1}$ |

The rate of inhibition of (TAL6003)-plasmin by α2-antiplasmin was determined to be 1.8±0.06×10$^7$ M$^{-1}$ s$^{-1}$ using the method of Wiman and Collen (Wiman, B. and D. Collen, *Eur. J. Biochem.* 84: 573-578 (1978)) in which plasmin and α2-antiplasmin are mixed then assayed for S-2251 activity at specific time points (Table 3). This value is comparable to reported values for plasmin of 2.5×10$^7$ M$^{-1}$ s$^{-1}$ (from Anonick, et al., *Thrombosis Res.* 59: 449 (1990)).

TABLE 3

Inhibition rates for various plasmin species and inhibitors were determined at 22° C. in PBS buffer, pH 7.4.

| | α$_2$-antiplasmin |
|---|---|
| plasmin | 2.5 ± 0.5 × 10$^7$ M$^{-1}$ s$^{-1}$ |
| mini-plasmin | 2.4 ± 0.5 × 10$^5$ M$^{-1}$ s$^{-1}$ |
| micro-plasmin | 1.8 ± 0.2 × 10$^5$ M$^{-1}$ s$^{-1}$ |
| (TAL6003)-plasmin | 1.8 ± 0.06 × 10$^7$ M$^{-1}$ s$^{-1}$ |

The same experiments conducted with micro-plasmin revealed α2-antiplasmin inhibition rates of 1.8×10$^5$ M$^{-1}$ s$^{-1}$ and 3.1×10$^5$ M$^{-1}$ s$^{-1}$ in two separate experiments. The rate of α2-antiplasmin inhibition of mini-plasmin (mini-plasmin domain composition, K5-SP) was determined to be 2.4×10$^5$ M$^{-1}$ s$^{-1}$. These data are in reasonable agreement with literature values for micro- and mini-plasmin and show that inhibition of (TAL6003)-plasmin by α2-antiplasmin is 40-fold faster than the inhibition of either micro-plasmin or mini-plasmin. Thus, these results indicate that (TAL6003)-plasmin should be rapidly inhibited by α2-antiplasmin due to the presence of kringle 1 in its structure. Overall, the data presented in this section show that the enzymatic and inhibitory properties of (TAL6003)-plasmin is similar to full-length plasmin.

Literature values are taken from Anonick, et al., *Thrombosis Res.* 59: 449 (1990). All rates were measured according to the methods published in Anonick, et al.

In Vitro Fibrinolytic Efficacy

The fibrinolytic efficacy of (TAL6003)-plasmin was tested in an in vitro model of clot lysis assay using the following experimental protocol.

In vitro comparison of the thrombolytic efficacy of (TAL6003)-plasmin with plasma-derived plasmin. Equimolar amounts of plasma-derived plasmin (0.25 mg/mL) and (TAL6003)-plasmin (0.11 mg/mL) were mixed with blood clots in the test tube and degree of clot lysis was monitored by A$_{280}$ absorbance of material released from the clot.

Figure 9:
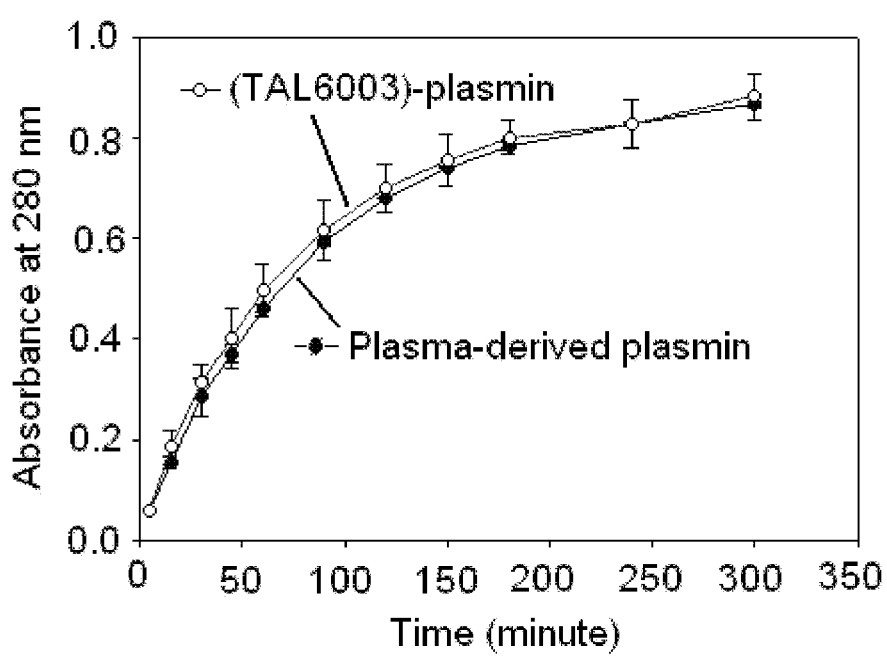
FIG. 9 shows in vitro comparison of the thrombolytic efficacy of (TAL6003)-plasmin with plasma-derived plasmin.

The concentrations of plasmin or (TAL6003)-plasmin required to overcome plasma inhibitors in the presence of fibrin and initiate clot lysis are shown in FIG. 9.

What is claimed is:

1. A method for making a recombinant plasmin polypeptide, the method comprising:
   (a) providing a polypeptide having a single N-terminal kringle domain wherein the last four amino acid residues within the kringle domain are identical to residues at positions 91-94 of SEQ ID NO: 2; and a C-terminal domain activation site and serine protease domain; wherein the polypeptide binds to immobilized lysine; and wherein the polypeptide is at least 95% identical to the sequence shown in SEQ ID NO: 2;
   (b) contacting the polypeptide provided in step (a) with a protease under conditions sufficient to cleave one or more peptide bonds thereby forming an active recombinant plasmin polypeptide.

2. The method of claim 1, wherein the polypeptide has an amino acid sequence shown in SEQ ID NO: 2.

3. The method of claim 1, wherein providing comprises expressing a DNA sequence shown in SEQ ID NO: 1, or a degenerate variant thereof, in E. coli.

4. The method of claim 1, wherein the polypeptide is at least 98% identical to the sequence shown in SEQ ID NO: 2.

5. The method of claim 1, wherein amino acid residues 2-9 of the polypeptide are identical to residues at positions 2-9 of SEQ ID: NO: 2.

6. The method of claim 1, wherein the polypeptide has the amino acid sequence shown in SEQ ID NO: 2 with no more than 15 amino acid substitutions.

7. The method of claim 1, wherein the polypeptide has the amino acid sequence shown in SEQ ID NO: 2 with no more than 10 amino acid substitutions.

8. The method of claim 1 wherein the polypeptide has the amino acid sequence shown in SEQ ID NO: 2 with no more than 8 amino acid substitutions.

9. The method of claim 1, wherein the polypeptide has the amino acid sequence shown in SEQ ID NO: 2 with no more than 5 amino acid substitutions.

10. The method of claim 1, wherein the polypeptide has the amino acid sequence shown in SEQ ID NO: 2 with no more than 3 amino acid substitutions.

11. The method of claim 1, wherein the polypeptide exhibits a lower binding affinity for fibrinogen than the binding affinity for fibrinogen of mini-plasmin.

12. The method of claim 1, wherein the polypeptide exhibits higher binding affinity for partially cleaved fibrin than the binding affinity for partially cleaved fibrin of mini-plasmin.

13. The method of claim 1, wherein the polypeptide exhibits a fibrinolytic activity that is inhibited by α2-antiplasmin at a rate of inhibition that is at least about 5-fold faster than the rate of inhibition of the fibrinolytic activity of mini-plasmin by α2-antiplasmin.

14. The method of claim 1, wherein the rate of inhibition is at least 10-fold to 40-fold faster than the rate of inhibition of miniplasmin.

15. The method of claim 1, wherein the immobilized lysine is lysine bound to a solid support matrix selected from the group consisting of lysine-agarose, lysine-hydrogel, and lysine-cross-linked agarose.

16. The method of claim 14, wherein the immobilized lysine is lysine-cross-linked agarose.

17. The method of claim 1, wherein the polypeptide has reduced immunogenicity as compared to a reference polypeptide, wherein the reference polypeptide has a primary amino acid sequence identical to the primary amino acid sequence of the polypeptide; with the proviso that the last four amino acid residues of the single N-terminal kringle domain of the reference polypeptide are not identical to residues at positions 91-94 of SEQ ID NO: 2.

18. The method of claim 1, wherein the protease is streptokinase, urokinase, or tissue plasminogen activator (tPA).

19. The method of claim 1, wherein the protease is streptokinase.

* * * * *

SEQUENCE LISTING

```
<160> NUMBER OF SEQ ID NOS: 15

<210> SEQ ID NO 1
<211> LENGTH: 1032
<212> TYPE: DNA
<213> ORGANISM: Artificial Sequence
<220> FEATURE:
```

<223> OTHER INFORMATION: Nucleotide sequence encoding a polypeptide having a single N-terminal kringle domain homologous to a kringle domain of a native human plasminogen

<400> SEQUENCE: 1

```
atgcgtgatg tcgtcttatt cgagaagaaa gtctatttat ctgaatgtaa aacaggcaat     60
ggtaaaaact atcgcggtac catgtccaaa acaaaaaacg gtatcacttg tcaaaaatgg    120
tctagcactt cacccatcg tcctcgtttc tcccctgcga cccatccctc tgaaggcctc     180
gaagaaaact actgccgcaa ccccgataat gatcctcaag gcccatggtg ttatactacc    240
gatcctgaaa aacgttatga ctattgcgat gtcccacaat gcgcagcccc ttcttttgat    300
tgcggcaaac cacaagttga acccaagaaa tgtccaggtc gtgttgtcgg cggttgtgtt    360
gcgcatcccc acagttggcc gtggcaggtc tcattacgta cccggtttgg aatgcacttt    420
tgtggcggca ctctcatctc gcccgaatgg gttcttacag ctgcacactg tttggaaaaa    480
agcccccgtc cttcttctta taaagttatc ctcggcgcac atcaagaagt caatttagaa    540
cctcatgtac aagaaatcga agtatctcgt ttattcctgg aaccgactcg caaagacatc    600
gcattactta aactgcctc cccgctgtg atcaccgata agtaattcc cgcgtgttta     660
ccttctccta attatgttgt tgcagatcgt acagaatgct ttattaccgg ctggggtgaa    720
actcaaggta cttttggtgc gggactcctg aaagaagcac agttaccagt catcgaaaac    780
aaagtatgta atcgctacga attcttaaac ggtcgtgttc aatccacaga attgtgcgca    840
ggtcatttag caggtggcac tgatagctgt caaggtgatt caggtggtcc tctcgtatgt    900
ttcgaaaaag ataaatatat tctgcaaggc gtcacctctt ggggtttagg ttgtgctcgt    960
cccaataaac ctggtgtata tgtacgtgta agtcgttttg ttacctggat tgaaggtgtt   1020
atgcggaaca ac                                                       1032
```

<210> SEQ ID NO 2
<211> LENGTH: 344
<212> TYPE: PRT
<213> ORGANISM: Artificial Sequence
<220> FEATURE:
<223> OTHER INFORMATION: Polypeptide having a single N-terminal kringle domain homologous to a kringle domain of a native human plasminogen

<400> SEQUENCE: 2

```
Met Arg Asp Val Val Leu Phe Glu Lys Lys Val Tyr Leu Ser Glu Cys
1               5                  10                  15

Lys Thr Gly Asn Gly Lys Asn Tyr Arg Gly Thr Met Ser Lys Thr Lys
            20                  25                  30

Asn Gly Ile Thr Cys Gln Lys Trp Ser Ser Thr Ser Pro His Arg Pro
        35                  40                  45

Arg Phe Ser Pro Ala Thr His Pro Ser Glu Gly Leu Glu Glu Asn Tyr
    50                  55                  60

Cys Arg Asn Pro Asp Asn Asp Pro Gln Gly Pro Trp Cys Tyr Thr Thr
65                  70                  75                  80

Asp Pro Glu Lys Arg Tyr Asp Tyr Cys Asp Val Pro Gln Cys Ala Ala
                85                  90                  95

Pro Ser Phe Asp Cys Gly Lys Pro Gln Val Glu Pro Lys Lys Cys Pro
            100                 105                 110

Gly Arg Val Val Gly Gly Cys Val Ala His Pro His Ser Trp Pro Trp
        115                 120                 125

Gln Val Ser Leu Arg Thr Arg Phe Gly Met His Phe Cys Gly Gly Thr
    130                 135                 140
```

| | | | | | | | | | | | | | | |
|---|---|---|---|---|---|---|---|---|---|---|---|---|---|---|
|Leu|Ile|Ser|Pro|Glu|Trp|Val|Leu|Thr|Ala|Ala|His|Cys|Leu|Glu|Lys|
|145| | | | |150| | | | |155| | | | |160|

| | | | | | | | | | | | | |
|---|---|---|---|---|---|---|---|---|---|---|---|---|
|Ser|Pro|Arg|Pro|Ser|Ser|Tyr|Lys|Val|Ile|Leu|Gly|Ala|His|Gln|Glu|
| | | | |165| | | | |170| | | | |175| |

|Val|Asn|Leu|Glu|Pro|His|Val|Gln|Glu|Ile|Glu|Val|Ser|Arg|Leu|Phe|
|---|---|---|---|---|---|---|---|---|---|---|---|---|---|---|---|
| | | |180| | | | |185| | | | |190| | |

|Leu|Glu|Pro|Thr|Arg|Lys|Asp|Ile|Ala|Leu|Leu|Lys|Leu|Ser|Ser|Pro|
|---|---|---|---|---|---|---|---|---|---|---|---|---|---|---|---|
| | |195| | | | |200| | | | |205| | | |

|Ala|Val|Ile|Thr|Asp|Lys|Val|Ile|Pro|Ala|Cys|Leu|Pro|Ser|Pro|Asn|
|---|---|---|---|---|---|---|---|---|---|---|---|---|---|---|---|
| |210| | | | |215| | | | |220| | | | |

|Tyr|Val|Val|Ala|Asp|Arg|Thr|Glu|Cys|Phe|Ile|Thr|Gly|Trp|Gly|Glu|
|---|---|---|---|---|---|---|---|---|---|---|---|---|---|---|---|
|225| | | | |230| | | | |235| | | | |240|

|Thr|Gln|Gly|Thr|Phe|Gly|Ala|Gly|Leu|Leu|Lys|Glu|Ala|Gln|Leu|Pro|
|---|---|---|---|---|---|---|---|---|---|---|---|---|---|---|---|
| | | | |245| | | | |250| | | | |255| |

|Val|Ile|Glu|Asn|Lys|Val|Cys|Asn|Arg|Tyr|Glu|Phe|Leu|Asn|Gly|Arg|
|---|---|---|---|---|---|---|---|---|---|---|---|---|---|---|---|
| | | |260| | | | |265| | | | |270| | |

|Val|Gln|Ser|Thr|Glu|Leu|Cys|Ala|Gly|His|Leu|Ala|Gly|Gly|Thr|Asp|
|---|---|---|---|---|---|---|---|---|---|---|---|---|---|---|---|
| | |275| | | | |280| | | | |285| | | |

|Ser|Cys|Gln|Gly|Asp|Ser|Gly|Gly|Pro|Leu|Val|Cys|Phe|Glu|Lys|Asp|
|---|---|---|---|---|---|---|---|---|---|---|---|---|---|---|---|
| |290| | | | |295| | | | |300| | | | |

|Lys|Tyr|Ile|Leu|Gln|Gly|Val|Thr|Ser|Trp|Gly|Leu|Gly|Cys|Ala|Arg|
|---|---|---|---|---|---|---|---|---|---|---|---|---|---|---|---|
|305| | | | |310| | | | |315| | | | |320|

|Pro|Asn|Lys|Pro|Gly|Val|Tyr|Val|Arg|Val|Ser|Arg|Phe|Val|Thr|Trp|
|---|---|---|---|---|---|---|---|---|---|---|---|---|---|---|---|
| | | | |325| | | | |330| | | | |335| |

|Ile|Glu|Gly|Val|Met|Arg|Asn|Asn|
|---|---|---|---|---|---|---|---|
| | | |340| | | | |

<210> SEQ ID NO 3
<211> LENGTH: 2430
<212> TYPE: DNA
<213> ORGANISM: Homo sapiens

<400> SEQUENCE: 3

```
atggaacata aggaagtggt tcttctactt cttttatttc tgaaatcagg tcaaggagag      60
cctctggatg actatgtgaa tacccagggg gcttcactgt tcagtgtcac taagaagcag     120
ctgggagcag aagtatagaa gaatgtgca gcaaaatgtg aggaggacga agaattcacc     180
tgcagggcat ccaatatcca gtaaagag caacaatgtg tgataatggc tgaaaacagg     240
aagtcctcca taatcattag gatgagagat gtagttttat ttgaaaagaa agtgtatctc     300
tcagagtgca agactgggaa tggaaagaac tacagaggga cgatgtccaa aacaaaaaat     360
ggcatcacct gtcaaaaatg gagttccact tctccccaca gacctagatt ctcacctgct     420
acacacccct cagagggact ggaggagaac tactgcagga atccagacaa cgatccgcag     480
gggccctggt gctatactac tgatccagaa aagagatatg actactgcga cattcttgag     540
tgtgaagagg aatgtatgca ttgcagtgga aaaactatg acggcaaaat tccaagacc     600
atgtctggac tggaatgcca ggcctggac tctcagagcc acacgctca tggatacatt     660
ccttccaaat ttccaaacaa gaacctgaag aagaattact gtcgtaaccc cgataggag     720
ctgcggcctt ggtgttttca caccgacccc aacaagcgct gggaactttg cgacatcccc     780
cgctgcacaa cacctccacc atcttctggt cccacctacc agtgtctgaa gggaacaggt     840
gaaaactatc gcgggaatgt ggctgttacc gtttccgggc acacctgtca gcactggagt     900
gcacagaccc ctcacacaca taacaggaca ccagaaaact tccctgcaa aaatttggat     960
```

-continued

```
gaaaactact gccgcaatcc tgacggaaaa agggcccca+ ggtgccatac aaccaacagc    1020
caagtgcggt gggagtactg taagataccg tcctgtgact cctccccagt atccacggaa    1080
caattggctc ccacagcacc acctgagcta accctgtgg tccaggactg ctaccatggt    1140
gatggacaga gctaccgagg cacatcctcc accaccacca caggaaagaa gtgtcagtct    1200
tggtcatcta tgacaccaca ccggcaccag aagacccag aaaactaccc aaatgctggc    1260
ctgacaatga actactgcag gaatccagat gccgataaag cccctggtg ttttaccaca    1320 gaccccagcg tcaggtggga gtactgcaac ctgaaaaaat gctcaggaac agaagcgagt    1380
gttgtagcac ctccgcctgt tgtcctgctt ccagatgtag agactccttc gaagaagac     1440 tgtatgtttg ggaatgggaa aggataccga ggcaagaggg cgaccactgt tactgggacg    1500
ccatgccagg actgggctgc ccaggagccc catagacaca gcatttcac tccagagaca     1560 aatccacggg cgggtctgga aaaaaattac tgccgtaacc ctgatggtga tgtaggtggt    1620
ccctggtgct acacgacaaa tccaagaaaa ctttacgact actgtgatgt ccctcagtgt    1680 gcggccctt catttgattg tgggaagcct caagtggagc cgaagaaatg tcctggaagg    1740
gttgtggggg ggtgtgtggc ccacccacat tcctggccct ggcaagtcag tcttagaaca    1800
aggtttggaa tgcacttctg tggaggcacc ttgatatccc cagagtgggt gttgactgct    1860
gcccactgct tggagaagtc cccaaggcct tcatcctaca aggtcatcct gggtgcacac    1920
caagaagtga atctcgaacc gcatgttcag gaaatagaag tgtctaggct gttcttggag    1980
cccacacgaa aagatattgc cttgctaaag ctaagcagtc ctgccgtcat cactgacaaa    2040
gtaatcccag cttgtctgcc atccccaaat tatgtggtcg ctgaccggac cgaatgtttc    2100
atcactggct ggggagaaac ccaaggtact tttggagctg gccttctcaa ggaagcccag    2160
ctccctgtga ttgagaataa agtgtgcaat cgctatgagt ttctgaatgg aagagtccaa    2220
tccaccgaac tctgtgctgg catttggcc ggaggcactg acagttgcca gggtgacagt    2280
ggaggtcctc tggtttgctt cgagaaggac aaatacattt tacaaggagt cacttcttgg    2340
ggtcttggct gtgcacgccc caataagcct ggtgtctatg ttcgtgtttc aaggtttgtt    2400
acttggattg agggagtgat gagaaataat                                     2430
```

<210> SEQ ID NO 4  
<211> LENGTH: 810  
<212> TYPE: PRT  
<213> ORGANISM: Homo sapiens

<400> SEQUENCE: 4

```
Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
```

```
            115                 120                 125
Ser Thr Ser Pro His Arg Pro Arg Phe Ser Pro Ala Thr His Pro Ser
130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                    165                 170                 175

Asp Ile Leu Glu Cys Glu Glu Cys Met His Cys Ser Gly Glu Asn
                180                 185                 190

Tyr Asp Gly Lys Ile Ser Lys Thr Met Ser Gly Leu Glu Cys Gln Ala
                195                 200                 205

Trp Asp Ser Gln Ser Pro His Ala His Gly Tyr Ile Pro Ser Lys Phe
210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                    245                 250                 255

Cys Asp Ile Pro Arg Cys Thr Thr Pro Pro Ser Ser Gly Pro Thr
                260                 265                 270

Tyr Gln Cys Leu Lys Gly Thr Gly Glu Asn Tyr Arg Gly Asn Val Ala
                275                 280                 285

Val Thr Val Ser Gly His Thr Cys Gln His Trp Ser Ala Gln Thr Pro
290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                    325                 330                 335

Thr Thr Asn Ser Gln Val Arg Trp Glu Tyr Cys Lys Ile Pro Ser Cys
                340                 345                 350

Asp Ser Ser Pro Val Ser Thr Glu Gln Leu Ala Pro Thr Ala Pro Pro
                355                 360                 365

Glu Leu Thr Pro Val Val Gln Asp Cys Tyr His Gly Asp Gly Gln Ser
370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                    405                 410                 415

Pro Asn Ala Gly Leu Thr Met Asn Tyr Cys Arg Asn Pro Asp Ala Asp
                420                 425                 430

Lys Gly Pro Trp Cys Phe Thr Thr Asp Pro Ser Val Arg Trp Glu Tyr
                435                 440                 445

Cys Asn Leu Lys Lys Cys Ser Gly Thr Glu Ala Ser Val Val Ala Pro
                450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                    485                 490                 495

Val Thr Gly Thr Pro Cys Gln Asp Trp Ala Ala Gln Glu Pro His Arg
                500                 505                 510

His Ser Ile Phe Thr Pro Glu Thr Asn Pro Arg Ala Gly Leu Glu Lys
                515                 520                 525

Asn Tyr Cys Arg Asn Pro Asp Gly Asp Val Gly Gly Pro Trp Cys Tyr
                530                 535                 540
```

```
Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
                660                 665                 670

Ser Pro Ala Val Ile Thr Asp Lys Val Ile Pro Ala Cys Leu Pro Ser
            675                 680                 685

Pro Asn Tyr Val Val Ala Asp Arg Thr Glu Cys Phe Ile Thr Gly Trp
690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
                740                 745                 750

Thr Asp Ser Cys Gln Gly Asp Ser Gly Gly Pro Leu Val Cys Phe Glu
            755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
            805                 810

<210> SEQ ID NO 5
<211> LENGTH: 334
<212> TYPE: PRT
<213> ORGANISM: Artificial Sequence
<220> FEATURE:
<223> OTHER INFORMATION: Polypeptide having a single N-terminal kringle
      domain homologous to a kringle domain of a native human
      plasminogen

<400> SEQUENCE: 5

Val Tyr Leu Ser Glu Cys Lys Thr Gly Asn Gly Lys Asn Tyr Arg Gly
1               5                   10                  15

Thr Met Ser Lys Thr Lys Asn Gly Ile Thr Cys Gln Lys Trp Ser Ser
                20                  25                  30

Thr Ser Pro His Arg Pro Arg Phe Ser Pro Ala Thr His Pro Ser Glu
            35                  40                  45

Gly Leu Glu Glu Asn Tyr Cys Arg Asn Pro Asp Asn Asp Pro Gln Gly
        50                  55                  60

Pro Trp Cys Tyr Thr Thr Asp Pro Glu Lys Arg Tyr Asp Tyr Cys Asp
65                  70                  75                  80

Val Pro Gln Cys Ala Ala Pro Ser Phe Asp Cys Gly Lys Pro Gln Val
                85                  90                  95
```

-continued

```
Glu Pro Lys Lys Cys Pro Gly Arg Val Val Gly Gly Cys Val Ala His
            100                 105                 110
Pro His Ser Trp Pro Trp Gln Val Ser Leu Arg Thr Arg Phe Gly Met
            115                 120                 125
His Phe Cys Gly Gly Thr Leu Ile Ser Pro Glu Trp Val Leu Thr Ala
        130                 135                 140
Ala His Cys Leu Glu Lys Ser Pro Arg Pro Ser Ser Tyr Lys Val Ile
145                 150                 155                 160
Leu Gly Ala His Gln Glu Val Asn Leu Glu Pro His Val Gln Glu Ile
                165                 170                 175
Glu Val Ser Arg Leu Phe Leu Glu Pro Thr Arg Lys Asp Ile Ala Leu
            180                 185                 190
Leu Lys Leu Ser Ser Pro Ala Val Ile Thr Asp Lys Val Ile Pro Ala
            195                 200                 205
Cys Leu Pro Ser Pro Asn Tyr Val Val Ala Asp Arg Thr Glu Cys Phe
        210                 215                 220
Ile Thr Gly Trp Gly Glu Thr Gln Gly Thr Phe Gly Ala Gly Leu Leu
225                 230                 235                 240
Lys Glu Ala Gln Leu Pro Val Ile Glu Asn Lys Val Cys Asn Arg Tyr
                245                 250                 255
Glu Phe Leu Asn Gly Arg Val Gln Ser Thr Glu Leu Cys Ala Gly His
            260                 265                 270
Leu Ala Gly Gly Thr Asp Ser Cys Gln Gly Asp Ser Gly Gly Pro Leu
        275                 280                 285
Val Cys Phe Glu Lys Asp Lys Tyr Ile Leu Gln Gly Val Thr Ser Trp
290                 295                 300
Gly Leu Gly Cys Ala Arg Pro Asn Lys Pro Gly Val Tyr Val Arg Val
305                 310                 315                 320
Ser Arg Phe Val Thr Trp Ile Glu Gly Val Met Arg Asn Asn
                325                 330

<210> SEQ ID NO 6
<211> LENGTH: 79
<212> TYPE: PRT
<213> ORGANISM: Homo sapiens
<220> FEATURE:
<221> NAME/KEY: Kringle1
<222> LOCATION: (1)..(79)

<400> SEQUENCE: 6

Cys Lys Thr Gly Asn Gly Lys Asn Tyr Arg Gly Thr Met Ser Lys Thr
1               5                   10                  15
Lys Asn Gly Ile Thr Cys Gln Lys Trp Ser Ser Thr Ser Pro His Arg
            20                  25                  30
Pro Arg Phe Ser Pro Ala Thr His Pro Ser Glu Gly Leu Glu Glu Asn
        35                  40                  45
Tyr Cys Arg Asn Pro Asp Asn Asp Pro Gln Gly Pro Trp Cys Tyr Thr
    50                  55                  60
Thr Asp Pro Glu Lys Arg Tyr Asp Tyr Cys Asp Ile Leu Glu Cys
65                  70                  75

<210> SEQ ID NO 7
<211> LENGTH: 78
<212> TYPE: PRT
<213> ORGANISM: Homo sapiens
<220> FEATURE:
<221> NAME/KEY: Kringle2
<222> LOCATION: (1)..(78)
```

<400> SEQUENCE: 7

Cys Met His Cys Ser Gly Glu Asn Tyr Asp Gly Lys Ile Ser Lys Thr
1               5                   10                  15

Met Ser Gly Leu Glu Cys Gln Ala Trp Asp Ser Gln Ser Pro His Ala
            20                  25                  30

His Gly Tyr Ile Pro Ser Lys Phe Pro Asn Lys Asn Leu Lys Lys Asn
        35                  40                  45

Tyr Cys Arg Asn Pro Asp Arg Glu Leu Arg Pro Trp Cys Phe Thr Thr
    50                  55                  60

Asp Pro Asn Lys Arg Trp Glu Leu Cys Asp Ile Pro Arg Cys
65                  70                  75

<210> SEQ ID NO 8
<211> LENGTH: 78
<212> TYPE: PRT
<213> ORGANISM: Homo sapiens
<220> FEATURE:
<221> NAME/KEY: Kringle3
<222> LOCATION: (1)..(78)

<400> SEQUENCE: 8

Cys Leu Lys Gly Thr Gly Glu Asn Tyr Arg Gly Asn Val Ala Val Thr
1               5                   10                  15

Val Ser Gly His Thr Cys Gln His Trp Ser Ala Gln Thr Pro His Thr
            20                  25                  30

His Asn Arg Thr Pro Glu Asn Phe Pro Cys Lys Asn Leu Asp Glu Asn
        35                  40                  45

Tyr Cys Arg Asn Pro Asp Gly Lys Arg Ala Pro Trp Cys His Thr Thr
    50                  55                  60

Asn Ser Gln Val Arg Trp Glu Tyr Cys Lys Ile Pro Ser Cys
65                  70                  75

<210> SEQ ID NO 9
<211> LENGTH: 78
<212> TYPE: PRT
<213> ORGANISM: Homo sapiens
<220> FEATURE:
<221> NAME/KEY: Kringle4
<222> LOCATION: (1)..(78)

<400> SEQUENCE: 9

Cys Tyr His Gly Asp Gly Gln Ser Tyr Arg Gly Thr Ser Ser Thr Thr
1               5                   10                  15

Thr Thr Gly Lys Lys Cys Gln Ser Trp Ser Ser Met Thr Pro His Arg
            20                  25                  30

His Gln Lys Thr Pro Glu Asn Tyr Pro Asn Ala Gly Leu Thr Met Asn
        35                  40                  45

Tyr Cys Arg Asn Pro Asp Ala Asp Lys Gly Pro Trp Cys Phe Thr Thr
    50                  55                  60

Asp Pro Ser Val Arg Trp Glu Tyr Cys Asn Leu Lys Lys Cys
65                  70                  75

<210> SEQ ID NO 10
<211> LENGTH: 80
<212> TYPE: PRT
<213> ORGANISM: Homo sapiens
<220> FEATURE:
<221> NAME/KEY: Kringle5
<222> LOCATION: (1)..(80)

<400> SEQUENCE: 10

```
Cys Met Phe Gly Asn Gly Lys Gly Tyr Arg Gly Lys Arg Ala Thr Thr
1               5                   10                  15

Val Thr Gly Thr Pro Cys Gln Asp Trp Ala Ala Gln Glu Pro His Arg
            20                  25                  30

His Ser Ile Phe Thr Pro Glu Thr Asn Pro Arg Ala Gly Leu Glu Lys
            35                  40                  45

Asn Tyr Cys Arg Asn Pro Asp Gly Asp Val Gly Gly Pro Trp Cys Tyr
    50                  55                  60

Thr Thr Asn Pro Arg Lys Leu Tyr Asp Tyr Cys Asp Val Pro Gln Cys
65                  70                  75                  80

<210> SEQ ID NO 11
<211> LENGTH: 335
<212> TYPE: PRT
<213> ORGANISM: Artificial Sequence
<220> FEATURE:
<223> OTHER INFORMATION: Polypeptide having a single N-terminal kringle
      domain homologous to a kringle domain of a native human
      plasminogen

<400> SEQUENCE: 11

Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
            35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Val Pro Gln Cys Ala Ala Pro Ser Phe Asp Cys Gly Lys Pro Gln
                85                  90                  95

Val Glu Pro Lys Lys Cys Pro Gly Arg Val Val Gly Gly Cys Val Ala
            100                 105                 110

His Pro His Ser Trp Pro Trp Gln Val Ser Leu Arg Thr Arg Phe Gly
            115                 120                 125

Met His Phe Cys Gly Gly Thr Leu Ile Ser Pro Glu Trp Val Leu Thr
130                 135                 140

Ala Ala His Cys Leu Glu Lys Ser Pro Arg Pro Ser Ser Tyr Lys Val
145                 150                 155                 160

Ile Leu Gly Ala His Gln Glu Val Asn Leu Glu Pro His Val Gln Glu
                165                 170                 175

Ile Glu Val Ser Arg Leu Phe Leu Glu Pro Thr Arg Lys Asp Ile Ala
            180                 185                 190

Leu Leu Lys Leu Ser Ser Pro Ala Val Ile Thr Asp Lys Val Ile Pro
            195                 200                 205

Ala Cys Leu Pro Ser Pro Asn Tyr Val Val Ala Asp Arg Thr Glu Cys
210                 215                 220

Phe Ile Thr Gly Trp Gly Glu Thr Gln Gly Thr Phe Gly Ala Gly Leu
225                 230                 235                 240

Leu Lys Glu Ala Gln Leu Pro Val Ile Glu Asn Lys Val Cys Asn Arg
                245                 250                 255

Tyr Glu Phe Leu Asn Gly Arg Val Gln Ser Thr Glu Leu Cys Ala Gly
            260                 265                 270

His Leu Ala Gly Gly Thr Asp Ser Cys Gln Gly Asp Ser Gly Gly Pro
```

```
              275                 280                 285
Leu Val Cys Phe Glu Lys Asp Lys Tyr Ile Leu Gln Gly Val Thr Ser
290                 295                 300

Trp Gly Leu Gly Cys Ala Arg Pro Asn Lys Pro Gly Val Tyr Val Arg
305                 310                 315                 320

Val Ser Arg Phe Val Thr Trp Ile Glu Gly Val Met Arg Asn Asn
                325                 330                 335

<210> SEQ ID NO 12
<211> LENGTH: 713
<212> TYPE: PRT
<213> ORGANISM: Homo sapiens

<400> SEQUENCE: 12

Val Tyr Leu Ser Glu Cys Lys Thr Gly Asn Gly Lys Asn Tyr Arg Gly
1               5                   10                  15

Thr Met Ser Lys Thr Lys Asn Gly Ile Thr Cys Gln Lys Trp Ser Ser
                20                  25                  30

Thr Ser Pro His Arg Pro Arg Phe Ser Pro Ala Thr His Pro Ser Glu
            35                  40                  45

Gly Leu Glu Glu Asn Tyr Cys Arg Asn Pro Asp Asn Asp Pro Gln Gly
        50                  55                  60

Pro Trp Cys Tyr Thr Thr Asp Pro Glu Lys Arg Tyr Asp Tyr Cys Asp
65                  70                  75                  80

Ile Leu Glu Cys Glu Glu Glu Cys Met His Cys Ser Gly Glu Asn Tyr
                85                  90                  95

Asp Gly Lys Ile Ser Lys Thr Met Ser Gly Leu Glu Cys Gln Ala Trp
                100                 105                 110

Asp Ser Gln Ser Pro His Ala His Gly Tyr Ile Pro Ser Lys Phe Pro
            115                 120                 125

Asn Lys Asn Leu Lys Lys Asn Tyr Cys Arg Asn Pro Asp Arg Glu Leu
        130                 135                 140

Arg Pro Trp Cys Phe Thr Thr Asp Pro Asn Lys Arg Trp Glu Leu Cys
145                 150                 155                 160

Asp Ile Pro Arg Cys Thr Thr Pro Pro Pro Ser Ser Gly Pro Thr Tyr
                165                 170                 175

Gln Cys Leu Lys Gly Thr Gly Glu Asn Tyr Arg Gly Asn Val Ala Val
            180                 185                 190

Thr Val Ser Gly His Thr Cys Gln His Trp Ser Ala Gln Thr Pro His
        195                 200                 205

Thr His Asn Arg Thr Pro Glu Asn Phe Pro Cys Lys Asn Leu Asp Glu
    210                 215                 220

Asn Tyr Cys Arg Asn Pro Asp Gly Lys Arg Ala Pro Trp Cys His Thr
225                 230                 235                 240

Thr Asn Ser Gln Val Arg Trp Glu Tyr Cys Lys Ile Pro Ser Cys Asp
                245                 250                 255

Ser Ser Pro Val Ser Thr Glu Gln Leu Ala Pro Thr Ala Pro Pro Glu
            260                 265                 270

Leu Thr Pro Val Val Gln Asp Cys Tyr His Gly Asp Gly Gln Ser Tyr
        275                 280                 285

Arg Gly Thr Ser Ser Thr Thr Thr Thr Gly Lys Lys Cys Gln Ser Trp
    290                 295                 300

Ser Ser Met Thr Pro His Arg His Gln Lys Thr Pro Glu Asn Tyr Pro
305                 310                 315                 320

Asn Ala Gly Leu Thr Met Asn Tyr Cys Arg Asn Pro Asp Ala Asp Lys
```

```
                    325                 330                 335
Gly Pro Trp Cys Phe Thr Thr Asp Pro Ser Val Arg Trp Glu Tyr Cys
                340                 345                 350
Asn Leu Lys Lys Cys Ser Gly Thr Glu Ala Ser Val Ala Pro Pro
            355                 360                 365
Pro Val Val Leu Leu Pro Asp Val Glu Thr Pro Ser Glu Glu Asp Cys
    370                 375                 380
Met Phe Gly Asn Gly Lys Gly Tyr Arg Gly Lys Arg Ala Thr Thr Val
385                 390                 395                 400
Thr Gly Thr Pro Cys Gln Asp Trp Ala Ala Gln Glu Pro His Arg His
                405                 410                 415
Ser Ile Phe Thr Pro Glu Thr Asn Pro Arg Ala Gly Leu Glu Lys Asn
            420                 425                 430
Tyr Cys Arg Asn Pro Asp Gly Asp Val Gly Gly Pro Trp Cys Tyr Thr
                435                 440                 445
Thr Asn Pro Arg Lys Leu Tyr Asp Tyr Cys Asp Val Pro Gln Cys Ala
            450                 455                 460
Ala Pro Ser Phe Asp Cys Gly Lys Pro Gln Val Glu Pro Lys Lys Cys
465                 470                 475                 480
Pro Gly Arg Val Val Gly Gly Cys Val Ala His Pro His Ser Trp Pro
                485                 490                 495
Trp Gln Val Ser Leu Arg Thr Arg Phe Gly Met His Phe Cys Gly Gly
            500                 505                 510
Thr Leu Ile Ser Pro Glu Trp Val Leu Thr Ala Ala His Cys Leu Glu
            515                 520                 525
Lys Ser Pro Arg Pro Ser Ser Tyr Lys Val Ile Leu Gly Ala His Gln
530                 535                 540
Glu Val Asn Leu Glu Pro His Val Gln Glu Ile Glu Val Ser Arg Leu
545                 550                 555                 560
Phe Leu Glu Pro Thr Arg Lys Asp Ile Ala Leu Leu Lys Leu Ser Ser
                565                 570                 575
Pro Ala Val Ile Thr Asp Lys Val Ile Pro Ala Cys Leu Pro Ser Pro
            580                 585                 590
Asn Tyr Val Val Ala Asp Arg Thr Glu Cys Phe Ile Thr Gly Trp Gly
            595                 600                 605
Glu Thr Gln Gly Thr Phe Gly Ala Gly Leu Leu Lys Glu Ala Gln Leu
            610                 615                 620
Pro Val Ile Glu Asn Lys Val Cys Asn Arg Tyr Glu Phe Leu Asn Gly
625                 630                 635                 640
Arg Val Gln Ser Thr Glu Leu Cys Ala Gly His Leu Ala Gly Gly Thr
                645                 650                 655
Asp Ser Cys Gln Gly Asp Ser Gly Gly Pro Leu Val Cys Phe Glu Lys
                660                 665                 670
Asp Lys Tyr Ile Leu Gln Gly Val Thr Ser Trp Gly Leu Gly Cys Ala
            675                 680                 685
Arg Pro Asn Lys Pro Gly Val Tyr Val Arg Val Ser Arg Phe Val Thr
            690                 695                 700
Trp Ile Glu Gly Val Met Arg Asn Asn
705                 710
```

<210> SEQ ID NO 13
<211> LENGTH: 714
<212> TYPE: PRT
<213> ORGANISM: Homo sapiens

<400> SEQUENCE: 13

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro Asp Val Glu Thr Pro Ser Glu Glu Asp
    370                 375                 380

Cys Met Phe Gly Asn Gly Lys Gly Tyr Arg Gly Lys Arg Ala Thr Thr
385                 390                 395                 400

Val Thr Gly Thr Pro Cys Gln Asp Trp Ala Ala Gln Glu Pro His Arg
                405                 410                 415
```

```
His Ser Ile Phe Thr Pro Glu Thr Asn Pro Arg Ala Gly Leu Glu Lys
            420                 425                 430

Asn Tyr Cys Arg Asn Pro Asp Gly Asp Val Gly Gly Pro Trp Cys Tyr
            435                 440                 445

Thr Thr Asn Pro Arg Lys Leu Tyr Asp Tyr Cys Asp Val Pro Gln Cys
450                 455                 460

Ala Ala Pro Ser Phe Asp Cys Gly Lys Pro Gln Val Glu Pro Lys Lys
465                 470                 475                 480

Cys Pro Gly Arg Val Val Gly Cys Val Ala His Pro His Ser Trp
                485                 490                 495

Pro Trp Gln Val Ser Leu Arg Thr Arg Phe Gly Met His Phe Cys Gly
            500                 505                 510

Gly Thr Leu Ile Ser Pro Glu Trp Val Leu Thr Ala Ala His Cys Leu
            515                 520                 525

Glu Lys Ser Pro Arg Pro Ser Ser Tyr Lys Val Ile Leu Gly Ala His
            530                 535                 540

Gln Glu Val Asn Leu Glu Pro His Val Gln Glu Ile Glu Val Ser Arg
545                 550                 555                 560

Leu Phe Leu Glu Pro Thr Arg Lys Asp Ile Ala Leu Leu Lys Leu Ser
                565                 570                 575

Ser Pro Ala Val Ile Thr Asp Lys Val Ile Pro Ala Cys Leu Pro Ser
            580                 585                 590

Pro Asn Tyr Val Val Ala Asp Arg Thr Glu Cys Phe Ile Thr Gly Trp
            595                 600                 605

Gly Glu Thr Gln Gly Thr Phe Gly Ala Gly Leu Leu Lys Glu Ala Gln
            610                 615                 620

Leu Pro Val Ile Glu Asn Lys Val Cys Asn Arg Tyr Glu Phe Leu Asn
625                 630                 635                 640

Gly Arg Val Gln Ser Thr Glu Leu Cys Ala Gly His Leu Ala Gly Gly
                645                 650                 655

Thr Asp Ser Cys Gln Gly Asp Ser Gly Gly Pro Leu Val Cys Phe Glu
            660                 665                 670

Lys Asp Lys Tyr Ile Leu Gln Gly Val Thr Ser Trp Gly Leu Gly Cys
            675                 680                 685

Ala Arg Pro Asn Lys Pro Gly Val Tyr Val Arg Val Ser Arg Phe Val
            690                 695                 700

Thr Trp Ile Glu Gly Val Met Arg Asn Asn
705                 710

<210> SEQ ID NO 14
<211> LENGTH: 723
<212> TYPE: PRT
<213> ORGANISM: Homo sapiens

<400> SEQUENCE: 14

Met Arg Asp Val Val Leu Phe Glu Lys Lys Val Tyr Leu Ser Glu Cys
1               5                   10                  15

Lys Thr Gly Asn Gly Lys Asn Tyr Arg Gly Thr Met Ser Lys Thr Lys
            20                  25                  30

Asn Gly Ile Thr Cys Gln Lys Trp Ser Ser Thr Ser Pro His Arg Pro
        35                  40                  45

Arg Phe Ser Pro Ala Thr His Pro Ser Glu Gly Leu Glu Glu Asn Tyr
    50                  55                  60

Cys Arg Asn Pro Asp Asn Asp Pro Gln Gly Pro Trp Cys Tyr Thr Thr
65                  70                  75                  80
```

```
Asp Pro Glu Lys Arg Tyr Asp Tyr Cys Asp Ile Leu Glu Cys Glu Glu
                85                  90                  95

Glu Cys Met His Cys Ser Gly Glu Asn Tyr Asp Gly Lys Ile Ser Lys
            100                 105                 110

Thr Met Ser Gly Leu Glu Cys Gln Ala Trp Asp Ser Gln Ser Pro His
        115                 120                 125

Ala His Gly Tyr Ile Pro Ser Lys Phe Pro Asn Lys Asn Leu Lys Lys
    130                 135                 140

Asn Tyr Cys Arg Asn Pro Asp Arg Glu Leu Arg Pro Trp Cys Phe Thr
145                 150                 155                 160

Thr Asp Pro Asn Lys Arg Trp Glu Leu Cys Asp Ile Pro Arg Cys Thr
                165                 170                 175

Thr Pro Pro Pro Ser Ser Gly Pro Thr Tyr Gln Cys Leu Lys Gly Thr
            180                 185                 190

Gly Glu Asn Tyr Arg Gly Asn Val Ala Val Thr Val Ser Gly His Thr
        195                 200                 205

Cys Gln His Trp Ser Ala Gln Thr Pro His Thr His Asn Arg Thr Pro
    210                 215                 220

Glu Asn Phe Pro Cys Lys Asn Leu Asp Glu Asn Tyr Cys Arg Asn Pro
225                 230                 235                 240

Asp Gly Lys Arg Ala Pro Trp Cys His Thr Thr Asn Ser Gln Val Arg
                245                 250                 255

Trp Glu Tyr Cys Lys Ile Pro Ser Cys Asp Ser Ser Pro Val Ser Thr
            260                 265                 270

Glu Gln Leu Ala Pro Thr Ala Pro Pro Glu Leu Thr Pro Val Val Gln
        275                 280                 285

Asp Cys Tyr His Gly Asp Gly Gln Ser Tyr Arg Gly Thr Ser Ser Thr
    290                 295                 300

Thr Thr Thr Gly Lys Lys Cys Gln Ser Trp Ser Ser Met Thr Pro His
305                 310                 315                 320

Arg His Gln Lys Thr Pro Glu Asn Tyr Pro Asn Ala Gly Leu Thr Met
                325                 330                 335

Asn Tyr Cys Arg Asn Pro Asp Ala Asp Lys Gly Pro Trp Cys Phe Thr
            340                 345                 350

Thr Asp Pro Ser Val Arg Trp Glu Tyr Cys Asn Leu Lys Lys Cys Ser
        355                 360                 365

Gly Thr Glu Ala Ser Val Val Ala Pro Pro Val Val Leu Leu Pro
    370                 375                 380

Asp Val Glu Thr Pro Ser Glu Glu Asp Cys Met Phe Gly Asn Gly Lys
385                 390                 395                 400

Gly Tyr Arg Gly Lys Arg Ala Thr Thr Val Thr Gly Thr Pro Cys Gln
                405                 410                 415

Asp Trp Ala Ala Gln Glu Pro His Arg His Ser Ile Phe Thr Pro Glu
            420                 425                 430

Thr Asn Pro Arg Ala Gly Leu Glu Lys Asn Tyr Cys Arg Asn Pro Asp
        435                 440                 445

Gly Asp Val Gly Gly Pro Trp Cys Tyr Thr Thr Asn Pro Arg Lys Leu
    450                 455                 460

Tyr Asp Tyr Cys Asp Val Pro Gln Cys Ala Ala Pro Ser Phe Asp Cys
465                 470                 475                 480

Gly Lys Pro Gln Val Glu Pro Lys Lys Cys Pro Gly Arg Val Val Gly
                485                 490                 495

Gly Cys Val Ala His Pro His Ser Trp Pro Trp Gln Val Ser Leu Arg
            500                 505                 510
```

-continued

```
Thr Arg Phe Gly Met His Phe Cys Gly Gly Thr Leu Ile Ser Pro Glu
        515                 520                 525

Trp Val Leu Thr Ala Ala His Cys Leu Glu Lys Ser Pro Arg Pro Ser
530                 535                 540

Ser Tyr Lys Val Ile Leu Gly Ala His Gln Val Asn Leu Glu Pro
545                 550                 555                 560

His Val Gln Glu Ile Glu Val Ser Arg Leu Phe Leu Glu Pro Thr Arg
                    565                 570                 575

Lys Asp Ile Ala Leu Leu Lys Leu Ser Ser Pro Ala Val Ile Thr Asp
                580                 585                 590

Lys Val Ile Pro Ala Cys Leu Pro Ser Pro Asn Tyr Val Val Ala Asp
            595                 600                 605

Arg Thr Glu Cys Phe Ile Thr Gly Trp Gly Glu Thr Gln Gly Thr Phe
        610                 615                 620

Gly Ala Gly Leu Leu Lys Glu Ala Gln Leu Pro Val Ile Glu Asn Lys
625                 630                 635                 640

Val Cys Asn Arg Tyr Glu Phe Leu Asn Gly Arg Val Gln Ser Thr Glu
                    645                 650                 655

Leu Cys Ala Gly His Leu Ala Gly Gly Thr Asp Ser Cys Gln Gly Asp
                660                 665                 670

Ser Gly Gly Pro Leu Val Cys Phe Glu Lys Asp Lys Tyr Ile Leu Gln
            675                 680                 685

Gly Val Thr Ser Trp Gly Leu Gly Cys Ala Arg Pro Asn Lys Pro Gly
        690                 695                 700

Val Tyr Val Arg Val Ser Arg Phe Val Thr Trp Ile Glu Gly Val Met
705                 710                 715                 720

Arg Asn Asn

<210> SEQ ID NO 15
<211> LENGTH: 791
<212> TYPE: PRT
<213> ORGANISM: Homo sapiens

<400> SEQUENCE: 15

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Cys Ala Ala
                20                  25                  30

Lys Cys Glu Glu Asp Glu Glu Phe Thr Cys Arg Ala Phe Gln Tyr His
            35                  40                  45

Ser Lys Glu Gln Gln Cys Val Ile Met Ala Glu Asn Arg Lys Ser Ser
        50                  55                  60

Ile Ile Ile Arg Met Arg Asp Val Val Leu Phe Glu Lys Val Tyr
65                  70                  75                  80

Leu Ser Glu Cys Lys Thr Gly Asn Gly Lys Asn Tyr Arg Gly Thr Met
                    85                  90                  95

Ser Lys Thr Lys Asn Gly Ile Thr Cys Gln Lys Trp Ser Ser Thr Ser
                100                 105                 110

Pro His Arg Pro Arg Phe Ser Pro Ala Thr His Pro Ser Glu Gly Leu
            115                 120                 125

Glu Glu Asn Tyr Cys Arg Asn Pro Asp Asn Asp Pro Gln Gly Pro Trp
        130                 135                 140

Cys Tyr Thr Thr Asp Pro Glu Lys Arg Tyr Asp Tyr Cys Asp Ile Leu
145                 150                 155                 160
```

-continued

```
Glu Cys Glu Glu Glu Cys Met His Cys Ser Gly Asn Tyr Asp Gly
            165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
            195                 200                 205

Asn Leu Lys Lys Asn Tyr Cys Arg Asn Pro Asp Arg Glu Leu Arg Pro
        210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Ser Ser Gly Pro Thr Tyr Gln Cys
            245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
            275                 280                 285

Asn Arg Thr Pro Glu Asn Phe Pro Cys Lys Asn Leu Asp Glu Asn Tyr
            290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
            325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
            355                 360                 365

Thr Ser Ser Thr Thr Thr Thr Gly Lys Lys Cys Gln Ser Trp Ser Ser
            370                 375                 380

Met Thr Pro His Arg His Gln Lys Thr Pro Glu Asn Tyr Pro Asn Ala
385                 390                 395                 400

Gly Leu Thr Met Asn Tyr Cys Arg Asn Pro Asp Ala Asp Lys Gly Pro
            405                 410                 415

Trp Cys Phe Thr Thr Asp Pro Ser Val Arg Trp Glu Tyr Cys Asn Leu
            420                 425                 430

Lys Lys Cys Ser Gly Thr Glu Ala Ser Val Val Ala Pro Pro Pro Val
            435                 440                 445

Val Leu Leu Pro Asp Val Glu Thr Pro Ser Glu Glu Asp Cys Met Phe
    450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
            485                 490                 495

Phe Thr Pro Glu Thr Asn Pro Arg Ala Gly Leu Glu Lys Asn Tyr Cys
            500                 505                 510

Arg Asn Pro Asp Gly Asp Val Gly Gly Pro Trp Cys Tyr Thr Thr Asn
        515                 520                 525

Pro Arg Lys Leu Tyr Asp Tyr Cys Asp Val Pro Gln Cys Ala Ala Pro
            530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
            565                 570                 575

Val Ser Leu Arg Thr Arg Phe Gly Met His Phe Cys Gly Gly Thr Leu
            580                 585                 590
```

-continued

```
Ile Ser Pro Glu Trp Val Leu Thr Ala Ala His Cys Leu Glu Lys Ser
        595                 600                 605
Pro Arg Pro Ser Ser Tyr Lys Val Ile Leu Gly Ala His Gln Glu Val
        610                 615                 620
Asn Leu Glu Pro His Val Gln Glu Ile Glu Val Ser Arg Leu Phe Leu
625                 630                 635                 640
Glu Pro Thr Arg Lys Asp Ile Ala Leu Leu Lys Leu Ser Ser Pro Ala
                645                 650                 655
Val Ile Thr Asp Lys Val Ile Pro Ala Cys Leu Pro Ser Pro Asn Tyr
                660                 665                 670
Val Val Ala Asp Arg Thr Glu Cys Phe Ile Thr Gly Trp Gly Glu Thr
            675                 680                 685
Gln Gly Thr Phe Gly Ala Gly Leu Leu Lys Glu Ala Gln Leu Pro Val
        690                 695                 700
Ile Glu Asn Lys Val Cys Asn Arg Tyr Glu Phe Leu Asn Gly Arg Val
705                 710                 715                 720
Gln Ser Thr Glu Leu Cys Ala Gly His Leu Ala Gly Gly Thr Asp Ser
                725                 730                 735
Cys Gln Gly Asp Ser Gly Gly Pro Leu Val Cys Phe Glu Lys Asp Lys
            740                 745                 750
Tyr Ile Leu Gln Gly Val Thr Ser Trp Gly Leu Gly Cys Ala Arg Pro
        755                 760                 765
Asn Lys Pro Gly Val Tyr Val Arg Val Ser Arg Phe Val Thr Trp Ile
        770                 775                 780
Glu Gly Val Met Arg Asn Asn
785                 790
```